United States Patent
Tojo et al.

(10) Patent No.: US 11,351,402 B2
(45) Date of Patent: Jun. 7, 2022

(54) METHOD FOR PRODUCING COATING FILM

(71) Applicant: Kao Corporation, Tokyo (JP)

(72) Inventors: Takehiko Tojo, Utsunomiya (JP); Ikuo Fukuda, Chikusei (JP)

(73) Assignee: Kao Corporation, Tokyo (JP)

( * ) Notice: Subject to any disclaimer, the term of this patent is extended or adjusted under 35 U.S.C. 154(b) by 109 days.

(21) Appl. No.: 16/606,373

(22) PCT Filed: Apr. 19, 2018

(86) PCT No.: PCT/JP2018/016204
§ 371 (c)(1),
(2) Date: Oct. 18, 2019

(87) PCT Pub. No.: WO2018/194140
PCT Pub. Date: Oct. 25, 2018

(65) Prior Publication Data
US 2020/0129786 A1    Apr. 30, 2020

(30) Foreign Application Priority Data

Apr. 19, 2017 (JP) .............................. JP2017-083246
Apr. 19, 2017 (JP) .............................. JP2017-083247

(51) Int. Cl.
*B05D 1/04* (2006.01)
*B05D 1/06* (2006.01)
(Continued)

(52) U.S. Cl.
CPC .............. *A61Q 1/02* (2013.01); *A61Q 19/00* (2013.01); *B05D 1/005* (2013.01); *B05D 1/007* (2013.01);
(Continued)

(58) Field of Classification Search
CPC . A61Q 1/02; A61Q 1/12; A61Q 19/00; A61Q 15/00; A61Q 17/04; B05D 1/005;
(Continued)

(56) References Cited

U.S. PATENT DOCUMENTS 3,857,233 A    12/1974 Cardinal et al.
4,125,752 A    11/1978 Wegener
(Continued)

FOREIGN PATENT DOCUMENTS

CN    1638877 A  *  7/2005  .......... B05B 5/1691
CN    1638877 A      7/2005
(Continued)

OTHER PUBLICATIONS

International Search Report dated Jun. 26, 2018 in PCT/JP2018/016216, citing documents AO and AP therein, 2 pages.
(Continued)

*Primary Examiner* — Alexander M Weddle
(74) *Attorney, Agent, or Firm* — Oblon, McClelland, Maier & Neustadt, L.L.P.

(57) ABSTRACT

A method for producing a film of the present invention includes the step of electrostatically spraying a liquid composition directly on the surface of skin using an electrostatic spray device to form a film on the skin. The electrostatic spray device includes a container capable of storing the liquid composition, a nozzle configured to eject the liquid composition, a power supply configured to apply a voltage to the nozzle, and a voltage stabilizer configured to stabilize the voltage applied by the power supply to the nozzle. The liquid composition contains component (a): one or more volatile substances selected from alcohols and ketones, and component (b): a polymer having film formability.

11 Claims, 2 Drawing Sheets

(51) Int. Cl.
  *A61Q 1/02* (2006.01)
  *A61Q 19/00* (2006.01)
  *B05D 1/00* (2006.01)
  *A61K 8/34* (2006.01)
  *A61Q 1/12* (2006.01)
  *A61Q 15/00* (2006.01)
  *A61Q 17/04* (2006.01)

(52) U.S. Cl.
  CPC .................. *B05D 1/04* (2013.01); *A61K 8/34* (2013.01); *A61Q 1/12* (2013.01); *A61Q 15/00* (2013.01); *A61Q 17/04* (2013.01)

(58) Field of Classification Search
  CPC .......... B05D 1/007; B05D 1/04; B05B 5/006; B05B 5/007; B05B 5/053; B05B 5/1691; A61K 8/046; A61K 8/34; A61K 8/73; A61K 2800/95; D01D 5/0061; D01D 5/0038; D01D 5/0084; A61M 35/00
  See application file for complete search history.

(56) References Cited

U.S. PATENT DOCUMENTS

| | | | |
|---|---|---|---|
| 5,322,684 A | | 6/1994 | Barnett et al. |
| 5,945,111 A | | 8/1999 | Esser |
| 6,135,369 A | | 10/2000 | Prendergast et al. |
| 6,311,903 B1 | * | 11/2001 | Gaw ...................... A45D 34/00 239/690 |
| 6,381,109 B1 | * | 4/2002 | Burtin .................... H02H 7/003 361/20 |
| 6,461,626 B1 | * | 10/2002 | Rabe ........................ A61K 8/29 424/401 |
| 6,514,504 B1 | | 2/2003 | Yen et al. |
| 6,531,142 B1 | | 3/2003 | Rabe et al. |
| 7,105,058 B1 | | 9/2006 | Sinyagin |
| 2004/0094873 A1 | * | 5/2004 | Dubson .................. B29C 67/20 264/465 |
| 2005/0212879 A1 | | 9/2005 | Chiao et al. |
| 2007/0131805 A1 | | 6/2007 | Yamaguchi et al. |
| 2009/0200392 A1 | | 8/2009 | Duru et al. |
| 2009/0202616 A1 | * | 8/2009 | Chong ................. D01D 5/0084 424/447 |
| 2016/0030957 A1 | * | 2/2016 | Dau ....................... B05B 5/0255 239/3 |
| 2018/0317627 A1 | * | 11/2018 | Fukuda .................. A61K 8/046 |
| 2019/0053602 A1 | * | 2/2019 | Amari ..................... A61L 26/00 |
| 2019/0059551 A1 | * | 2/2019 | Amari ...................... A61K 8/34 |

FOREIGN PATENT DOCUMENTS

| | | | |
|---|---|---|---|
| CN | 1913975 A | 2/2007 | |
| EP | 3 366 270 A1 | 8/2018 | |
| EP | 3 375 323 A1 | 9/2018 | |
| JP | 2-78457 A | 3/1990 | |
| JP | 5-192224 A | 8/1993 | |
| JP | 2000-505356 A | 5/2000 | |
| JP | 2003-506474 A | 2/2003 | |
| JP | 2003-507166 A | 2/2003 | |
| JP | 2006-95332 A | 4/2006 | |
| JP | 2006-104211 A | 4/2006 | |
| JP | 2012-107364 A | 6/2012 | |
| JP | 2015-3293 A | 1/2015 | |
| JP | 2016-43306 A | 4/2016 | |
| JP | 2017-78062 A | 4/2017 | |
| JP | 2017-78063 A | 4/2017 | |
| TW | 193626 | 11/1992 | |
| WO | WO 94/11119 A1 | 5/1994 | |
| WO | WO 98/03267 A1 | 1/1998 | |
| WO | WO 01/12139 A1 | 2/2001 | |
| WO | WO 01/12335 A1 | 2/2001 | |
| WO | WO 03/072263 A1 | 9/2003 | |
| WO | WO-03072263 A1 * | 9/2003 | ........... B05B 5/1691 |
| WO | WO 2005/075095 A1 | 8/2005 | |
| WO | WO-2014141798 A1 * | 9/2014 | ........... B05B 5/0533 |
| WO | WO-2017069079 A1 * | 4/2017 | ........... D01D 5/0084 |
| WO | WO-2017069080 A1 * | 4/2017 | ............... A61K 8/31 |
| WO | WO-2017082179 A1 * | 5/2017 | ............. B05B 5/006 |

OTHER PUBLICATIONS

Extended European Search Report dated Dec. 14, 2020 in European Patent Application No. 18787349.2, citing documents AA, and AO through AR therein, 10 pages.

International Search Report dated Jun. 12, 2018 in PCT/JP2018/016204 filed on Apr. 19, 2018.

\* cited by examiner

METHOD FOR PRODUCING COATING FILM

CROSS REFERENCE TO RELATED APPLICATIONS

This application is a national phase application of PCT/JP2018/016204, filed Apr. 19, 2018, which claims priority to Japanese Patent Application No. 2017-083246, filed Apr. 19, 2017 and to Japanese Patent Application No. 2017-083247, filed Apr. 19, 2017, wherein the entire content and disclosure of each of the foregoing applications is incorporated herein by reference into the present application.

TECHNICAL FIELD

The present invention relates to a method for producing a film.

BACKGROUND ART

Various methods of forming a film by electrostatic spraying have been known. For example, Patent Literature 1 discloses a method of treating skin, and the method includes electrostatically spraying a composition on skin. The composition used in the method contains a liquid insulating material, a conductive material, a particulate material, and a thickener. The composition is typically a cosmetic containing a pigment or a skin care composition. Specifically, a cosmetic foundation is used as the composition. In other words, the invention according to Patent Literature 1 is intended to electrostatically spray a cosmetic foundation for beauty to thereby make up the skin.

Patent Literature 2 discloses a disposable cartridge used for an electrostatic spray device of cosmetics. The electrostatic spray device is a hand-held, self-contained device. The electrostatic spray device is used for spraying a cosmetic foundation as with Patent Literature 1.

Patent Literature 3 discloses a method of electrohydrodynamically forming a solid or gel substance containing a material having a biological activity on skin and a device used therefor. The device is a hand-held, portable device.

Patent Literature 4 intends stable mass production of nanofibers and discloses a method for producing nanofibers involving discharging and spinning a polymer solution under high-voltage application and a production device therefor.

CITATION LIST

Patent Literatures

Patent Literature 1: WO 01/12139 A1
Patent Literature 2: WO 01/12335 A1
Patent Literature 3: WO 98/03267 A1
Patent Literature 4: JP 2012-107364 A

SUMMARY OF INVENTION

The present invention relates to a method for producing a film, and the method includes the step of electrostatically spraying a liquid composition directly on a surface of skin using an electrostatic spray device to form a film on the skin. The electrostatic spray device includes
a container capable of storing the liquid composition,
a nozzle configured to eject the liquid composition,
a power supply configured to apply a voltage to the nozzle, and
a voltage stabilizer configured to stabilize the voltage applied by the power supply to the nozzle.
The liquid composition contains component (a) and component (b):
(a) one or more volatile substances selected from alcohols and ketones, and
(b) a polymer having film formability.

DESCRIPTION OF EMBODIMENTS

Figure 1:
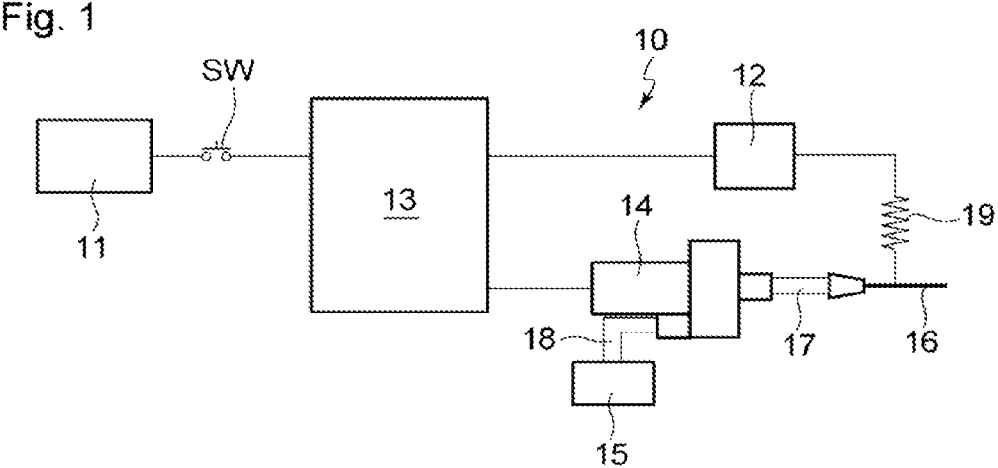
FIG. 1 is a schematic view showing a configuration of the electrostatic spray device used in the present invention.

When electrostatic spraying is performed to form a film on skin by the methods according to Patent Literatures 1 to 3, the film formed by the electrostatic spraying insufficiently adheres to the skin and may be damaged or peel off by an external force including friction. During film formation, the voltage applied to the film-forming liquid may be destabilized by the effect of ambient environment conditions including humidity, and this makes it difficult to stably form a film on skin.

The method according to Patent Literature 4 is for industrial production, and thus when electrostatic spraying is performed in accordance with the method in Patent Literature 4 to form a film on skin in a home or the like, where ambient environment conditions including humidity during production is difficult to control as compared with in factories, a stable voltage is failed to be applied in electrostatic spraying, and stable formation of a film on skin may be difficult.

The present invention therefore relates to a method of stably forming a film on skin irrespective of ambient environment conditions including humidity in electrostatic spraying.

The present invention will now be described on the basis of preferred embodiments thereof with reference to drawings. In the present invention, a composition containing prescribed components is applied directly onto skin to form a film. As the film formation method, an electrostatic spraying method is adopted in the present invention. In the electrostatic spraying method, a positive or negative high voltage is applied to a composition to electrically charge the composition, and the electrically charged composition is sprayed toward an object. The sprayed composition spreads in space while repeating miniaturization by the Coulomb repulsion. During this process or after the adhesion to an object, a solvent, which is a volatile substance, volatilizes, and a film is formed on the surface of the object.

In the present invention, the composition used in the electrostatic spraying method is liquid in an environment where the electrostatic spraying method is performed (hereinafter, the composition is also called "liquid composition"). The liquid composition contains the following component (a) and component (b):

(a) one or more volatile substances selected from the group consisting of alcohols and ketones; and (b) a polymer having film formability.

Hereinafter, the components will be described.

The volatile substance as the component (a) is a substance having volatility in a liquid state. In the liquid composition, the component (a) is contained for the following intention: the liquid composition in an electric field is sufficiently electrically charged and then is ejected from the tip of a nozzle toward skin; as the component (a) evaporates, the charge density of the liquid composition becomes excessive and thus the liquid composition is further miniaturized by Coulomb repulsion while the component (a) further evaporates; and consequently a dried film is formed. For this intention, the volatile substance preferably has a vapor pressure at 20° C. of 0.01 kPa or more and 106.66 kPa or less, more preferably 0.13 kPa or more and 66.66 kPa or less, even more preferably 0.67 kPa or more and 40.00 kPa or less, and further preferably 1.33 kPa or more and 40.00 kPa or less.

As the alcohol for the volatile substance as the component (a), for example, a monohydric chain aliphatic alcohol having 1 to 6 carbon atoms, a monohydric alicyclic alcohol having 3 to 6 carbon atoms, or a monohydric aromatic alcohol is suitably used. Specific examples thereof include ethanol, isopropyl alcohol, butyl alcohol, phenylethyl alcohol, propanol, and pentanol. One or more alcohols selected from these alcohols may be used.

As the ketone for the volatile substance as the component (a), for example, a chain aliphatic ketone having 3 to 6 carbon atoms, an alicyclic ketone having 3 to 6 carbon atoms, or an aromatic ketone having 8 to 10 carbon atoms is suitably used. Specific examples thereof include acetone, methyl ethyl ketone, methyl isobutyl ketone, cyclohexanone, and acetophenone. These ketones may be used singly or in combination of two or more of them.

The volatile substance as the component (a) is more preferably one or more substances selected from ethanol, isopropyl alcohol, butyl alcohol, and water, more preferably one or more substances selected from ethanol and butyl alcohol, and even more preferably ethanol.

The liquid composition contains, together with the component (a), a polymer having film formability as the component (b). The polymer having film formability as the component (b) is typically a substance capable of being dissolved in the volatile substance as the component (a). Here, "being dissolved" means that a substance is in a dispersion state at 20° C., and that the dispersion state is a visually uniform state, preferably a visually transparent or translucent state.

As the polymer having film formability, an appropriate polymer is used according to the properties of the volatile substance as the component (a). Specifically, the polymer having film formability is roughly classified into a water-soluble polymer and a water-insoluble polymer. The "water-soluble polymer" herein has the following properties: when 1 g of a polymer is weighed in an environment at 1 atmosphere and 23° C. and then is immersed in 10 g of ion-exchanged water for 24 hours, 0.5 g or more of the immersed polymer is dissolved in water. The "water-insoluble polymer" herein has the following properties: when 1 g of a polymer is weighed in an environment at 1 atmosphere and 23° C. and then is immersed in 10 g of ion-exchanged water for 24 hours, more than 0.5 g of the immersed polymer is not dissolved.

Examples of the water-soluble polymer having film formability include mucopolysaccharides such as pullulan, hyaluronic acid, chondroitin sulfate, poly-γ-glutamic acid, modified cornstarch, β-glucan, glucooligosaccharides, heparin, and keratosulfate; natural polymers such as cellulose, pectin, xylan, lignin, glucomannan, galacturonic acid, *psyllium* seed gum, tamarind seed gum, gum arabic, gum tragacanth, soybean water-soluble polysaccharides, alginic acid, carrageenan, laminaran, agar (agarose), fucoidan, methyl cellulose, hydroxypropyl cellulose, and hydroxypropyl methyl cellulose; and synthetic polymers such as a partially saponified polyvinyl alcohol (when used in combination with no crosslinking agent), a low-saponified polyvinyl alcohol, polyvinylpyrrolidone (PVP), polyethylene oxide, and sodium polyacrylate. These water-soluble polymers can be used singly or in combination of two or more of them. Of these water-soluble polymers, pullulan or a synthetic polymer such as a partially saponified polyvinyl alcohol, a low-saponified polyvinyl alcohol, polyvinylpyrrolidone, and polyethylene oxide is preferably used in view of easy production of a film. When used as the water-soluble polymer, the polyethylene oxide preferably has a number average molecular weight of 50,000 or more and 3,000,000 or less and more preferably 100,000 or more and 2,500,000 or less.

Examples of the water-insoluble polymer having film formability include a completely saponified polyvinyl alcohol that is to be insolubilized after film formation, a partially saponified polyvinyl alcohol that it to be crosslinked with a crosslinking agent after film formation, an oxazoline-modified silicone such as a poly(N-propanoylethyleneimine)-grafted dimethylsiloxane/γ-aminopropylmethylsiloxane copolymer, polyvinylacetal diethylaminoacetate, zein (major component of corn protein), polyester, polylactic acid (PLA), an acrylic resin such as a polyacrylonitrile resin and a polymethacrylate resin, a polystyrene resin, a polyvinyl butyral resin, a polyethylene terephthalate resin, a polybutylene terephthalate resin, a polyurethane resin such as polyurethane-64, a polyamide resin, a polyimide resin, and a polyamide imide resin. These water-insoluble polymers can be used singly or in combination of two or more of them. Of these water-insoluble polymers, a completely saponified polyvinyl alcohol that is to be insolubilized after film formation, a partially saponified polyvinyl alcohol that it so be crosslinked with a crosslinking agent after film formation, a polyvinyl butyral resin, a polymethacrylate resin, polyvinylacetal diethylaminoacetate, an oxazoline-modified silicone such as a poly(N-propanoylethyleneimine)-grafted dimethylsiloxane/γ-aminopropylmethylsiloxane copolymer, polylactic acid, zein, or the like is preferably used.

In the liquid composition, the content of the component (a) is preferably 50% by mass or more, more preferably 55% by mass or more, even more preferably 60% by mass or more, and further preferably 65% by mass or more. The content is preferably 95% by mass or less, more preferably 94% by mass or less, even more preferably 93% by mass or less, and further preferably 92% by mass or less. In the liquid composition, the content of the component (a) is preferably 50% by mass or more and 95% by mass or less, more preferably 55% by mass or more and 94% by mass or less, even more preferably 60% by mass or more and 93% by mass or less, and further preferably 65% by mass or more and 92% by mass or less, or is preferably 55% by mass or more and 92% by mass or less. The liquid composition having a content of the component (a) within the range described above can be sufficiently volatilized when the electrostatic spraying method is performed.

In the liquid composition, the content of the component (b) is preferably 1% by mass or more, more preferably 2% by mass or more, even more preferably 3% by mass or more, and further preferably 5% by mass or more. The content of the component (b) is preferably 40% by mass or less, and when the component (b) contains polyvinyl butyral, the content is preferably 35% by mass or less, more preferably 30% by mass or less, and even more preferably 25% by mass or less. In the liquid composition, the content of the component (b) is preferably 1% by mass or more and 40% by mass or less, is preferably 1% by mass or more and 35% by mass or less, more preferably 2% by mass or more and 35% by mass or less, even more preferably 3% by mass or more and 30% by mass or less, and further preferably 5% by mass or more and 25% by mass or less, or is preferably 5% by mass or more and 40% by mass or less. When the liquid composition has a content of the component (b) within the range described above, an intended film can be successfully formed.

The liquid composition may consist only of the component (a) and the component (b) described above or may further contain, in addition to the component (a) and the component (b), water as component (c). As the water, ion-exchanged water, purified water, or distilled water is suitably used.

When the liquid composition contains water as the component (c), the liquid composition has a higher conductivity due to ionization of water. When the liquid composition having a high conductivity is used to perform the electrostatic spraying described later, a fibrous film can be stably formed on the surface of an application site such as skin. Water also contributes to an improvement in adhesion of a film formed by electrostatic spraying to skin or the like.

In view of exhibiting such advantageous effects, the content of the component (c) in the liquid composition is preferably 0.2% by mass or more and 25% by mass or less. From the same viewpoint, the content of the component (c) in the liquid composition is preferably 0.3% by mass or more, more preferably 0.35% by mass or more, and even more preferably 0.4% by mass or more. In the liquid composition, the content of the component (c) is preferably 25% by mass or less, more preferably 20% by mass or less, even more preferably 19% by mass or less, and further preferably 18% by mass or less, in view of stable formability of a fibrous film. In the liquid composition, the content of the component (c) is preferably 0.2% by mass or more and 25% by mass or less, more preferably 0.3% by mass or more and 20% by mass or less, even more preferably 0.35% by mass or more and 19% by mass or less, and further preferably 0.4% by mass or more and 18% by mass or less, or is further preferably 0.3% by mass or more and 18% by mass or less.

In view of stable film formation by the electrostatic spraying method, the mass ratio of the content of the component (a) to that of the component (c), a/c, is preferably 3 or more, more preferably 3.5 or more, and even more preferably 4 or more. The mass ratio of the content of the component (a) to that of the component (c), a/c, is preferably 300 or less, more preferably 250 or less, and even more preferably 210 or less. The mass ratio of the content of the component (a) to that of the component (c), a/c, is preferably 3 or more and 300 or less, more preferably 3.5 or more and 250 or less, even more preferably 3.5 or more and 210 or less, and further preferably 4 or more and 210 or less.

From the same viewpoint, the mass ratio of the content of the component (b) to that of the component (c), b/c, is preferably 0.4 or more, more preferably 0.5 or more, and even more preferably 0.6 or more. The mass ratio of the content of the component (b) to that of the component (c), b/c, is preferably 140 or less, and when the component (b) contains polyvinyl butyral, the ratio is preferably 50 or less, more preferably 45 or less, and even more preferably 40 or less. The mass ratio of the content of the component (b) to that of the component (c), b/c, is preferably 0.4 or more and 140 or less, or is preferably 0.4 or more and 50 or less, more preferably 0.5 or more and 45 or less, and even more preferably 0.6 or more and 40 or less, or is preferably 0.6 or more and 140 or less.

In view of the dispersibility of the component (b) in the liquid composition and of an improvement of film formability, the mass ratio of the component (b) to the component (a), b/a, is preferably 0.01 or more, more preferably 0.02 or more, even more preferably 0.04 or more, and further preferably 0.07 or more. The mass ratio of the component (b) to the component (a), b/a, is preferably 0.70 or less, and when the component (b) contains polyvinyl butyral, the ratio is preferably 0.55 or less, more preferably 0.50 or less, even more preferably 0.30 or less, and further preferably 0.25 or less. Specifically, the mass ratio of the content of the component (b) to that of the component (a), b/a, is preferably 0.01 or more and 0.70 or less and more preferably 0.02 or more and 0.70 or less, or is preferably 0.01 or more and 0.55 or less, more preferably 0.02 or more and 0.50 or less, even more preferably 0.04 or more and 0.30 or less, and further preferably 0.07 or more and 0.25 or less.

The liquid composition may contain an additional component together with the component (a) and the component (b) or with the component (a), the component (b), and the component (c) described above. Examples of the additional component include a plasticizer for the polymer capable of forming a film as the component (b), a color pigment, an extender pigment, a dye, a surfactant, a UV protective agent, a fragrance chemical, a repellent, an antioxidant, a stabilizer, an antiseptic agent, and various vitamins. When the spraying composition contains an additional component, the content of the additional component is preferably 0.1% by mass or more and 30% by mass or less and more preferably 0.5% by mass or more and 20% by mass or less. When the liquid composition contains a powder component having a particle size of 0.1 μm or more at 20° C., such as a color pigment and an extender pigment, the content of the powder component is preferably 1% by mass or less, more preferably 0.5% by mass or less, and even more preferably 0.1% by mass or less in view of prevention of nozzle clogging of the electrostatic spray device described later and film adhesion. More preferably, the composition contains none of these powder components.

In particular, when the liquid composition contains the component (c), a salt can be further added as component (d) in view of an improvement in conductivity of the liquid composition and successful film formation by the electrostatic spraying method. In view of an improvement in conductivity, the component (d) is preferably an alkali metal salt or an ammonium salt. In view of a further improvement in dispersibility in the liquid composition containing the component (b) and of a further improvement in conductivity, the component (d) is preferably one or more compounds selected from ionic compounds and acylamino acid esters and more preferably one or more compounds selected from ionic surfactants, ionic polymers, betaine compounds, and acylamino acid esters.

Examples of the ionic surfactant include a cationic surfactant, an anionic surfactant, and an amphoteric surfactant.

The cationic surfactant is preferably a quaternary ammonium salt. The anionic surfactant is preferably an acylamino acid salt. The component (d) is more preferably one or more compounds selected from quaternary ammonium salts and acylamino acid salts.

Examples of the quaternary ammonium salt include a tetraalkylammonium salt, a benzylalkylammonium salt, a benzyltrialkylammonium salt, an alkylbenzyldimethylammonium salt, a mono-long-chain alkyltrimethylammonium salt, and a di-long-chain alkyldimethylammonium salt. Specific examples of the quaternary ammonium salt include cetyltrimethylammonium chloride, stearyltrimethylammonium chloride, behenyltrimethylammonium chloride, behenyldimethylhydroxyethylammonium chloride, distearyldiammonium chloride, stearyldimethylbenzylammonium chloride, di stearyldimethylammonium chloride, dicetylmethylammonium chloride, cetyltriethylammonium methylsulfate, and benzalkonium chloride.

Examples of the acylamino acid salt include an acyl glutamate, an acyl aspartate, an acyl sarcosinate, an acyl taurate, and an acyl methyltaurate, and the salt is preferably an alkali metal salt or an ammonium salt. Examples of the acylamino acid salt include sodium myristoyl glutamate, sodium myristoyl aspartate, sodium cocoyl glutamate, sodium lauroyl glutamate, sodium lauroyl aspartate, sodium lauroyl sarcosinate, and sodium palmitoyl sarcosinate.

Examples of the amphoteric surfactant include a betaine surfactant and a sulfobetaine surfactant and specifically include cocamide propyl betaine and cocamide propyl hydroxysultaine.

Examples of the ionic polymer include an anionic polymer, a cationic polymer, and an ampholytic polymer. Examples of the anionic polymer include a homopolymer or copolymer having a (meth)acrylic acid unit, including an acrylate/C1-18 alkyl acrylate/C1-8 alkyl acrylamide copolymer AMP. Examples of the cationic polymer include a homopolymer or copolymer having a primary to tertiary amino group or a quaternary ammonium group, including an ethyl acrylate/N-[3-(dimethylamino)propyl]acrylamide/N-tert-butylacrylamide/methacrylate-α-methyl-poly(oxyethylen)-ω-yl copolymer and a poly(N-propanoylethyleneimine)-grafted-dimethylsiloxane/γ-aminopropylmethylsiloxane copolymer monoethyl sulfate. Examples of the ampholytic polymer include a homopolymer or copolymer having an alkyl betaine unit or a sulfobetaine unit and specifically include an N-methylacryloyloxyethyl-N,N-dimethylammonium-α-N-methylcarboxybetaine/alkyl methacrylate copolymer.

Examples of the betaine compound include an amino acid compound having three methyl groups on an amino group, such as trimethylglycine, carnitine (vitamin Bt; 3-hydroxy-4-(trimethylammonio)butanoate ester), and an acylated carnitine.

Examples of the acylamino acid ester include an acylamino acid (phytosteryl/octyldodecyl) ester and specifically include di(phytosteryl/octyldodecyl) lauroyl glutamate.

In particular, the component (d) is preferably one or more compounds selected from cationic surfactants, anionic surfactants, amphoteric surfactants, acylamino acid esters, anionic polymers, cationic polymers, ampholytic polymers, and betaine compounds, and is more preferably one or more compounds selected from quaternary ammonium salts, acylamino acid salts, acylamino acid ester salts, homopolymers or copolymers having a (meth)acrylic acid unit, homopolymers or copolymers having a primary to tertiary amino group, homopolymers or copolymers having a quaternary ammonium group, homopolymers or copolymers having an alkyl betaine unit or a sulfobetaine unit, and trimethylglycine.

When a salt is further added as the component (d), the content of the component (d) in the liquid composition is preferably 0.01% by mass or more, more preferably 0.05% by mass or more, and even more preferably 0.1% by mass or more and is preferably 10% by mass or less, more preferably 8% by mass or less, even more preferably 6% by mass or less, further preferably 2.5% by mass or less, and furthermore preferably 2% by mass or less, in view of stable formation of a film and prevention of an excess increase in the conductivity described later. Specifically, the content of the component (d) is preferably 0.01% by mass or more and 10% by mass or less, more preferably 0.05% by mass or more and 8% by mass or less, and even more preferably 0.1% by mass or more and 6% by mass or less.

In view of film formability and an improvement in spinning stability, the mass ratio of the content of the component (d) to that of the component (c), d/c, is preferably 0.01 or more, more preferably 0.02 or more, and even more preferably 0.03 or more and is preferably 6 or less, more preferably 5 or less, and even more preferably 4 or less. Specifically, the mass ratio of the content of the component (d) to the component (c), d/c, is preferably 0.01 or more and 6 or less, more preferably 0.02 or more and 5 or less, and even more preferably 0.03 or more and 4 or less.

In view of stable formation of a film on skin, the liquid composition for the electrostatic spraying method preferably has a conductivity at 25° C. of 8 µS/cm or more, more preferably 10 µS/cm or more, even more preferably 20 µS/cm or more, further preferably 25 µS/cm or more, and furthermore preferably 50 µS/cm or more. From the same viewpoint, the liquid composition preferably has a conductivity of 300 µS/cm or less, more preferably 260 µS/cm or less, even more preferably 220 µS/cm or less, and further preferably 200 µS/cm or less. More specifically, the liquid composition preferably has a conductivity at 25° C. of 8 µS/cm or more and 300 µS/cm or less, and more preferably 8 µS/cm or more and 260 µS/cm or less, or is preferably 10 µS/cm or more and 300 µS/cm or less, more preferably 20 µS/cm or more and 260 µS/cm or less, even more preferably 25 µS/cm or more and 220 µS/cm or less, and further preferably 50 µS/cm or more and 200 µS/cm or less. The conductivity of a liquid composition can be determined using an impedance analyzer (SI1260, manufactured by Solartron) with a measurement terminal (SH-Z), in conditions of 25° C., ϕ10 mm, and a distance of 1 mm. The conductivity of the liquid composition at 25° C. can be appropriately adjusted by changing the mixing ratios of the component (a), the component (b), the component (c), and/or the component (d), provided that the above contents of the components are satisfied.

The liquid composition used in the electrostatic spraying method preferably has a viscosity at 25° C. of 5 mPa·s or more, more preferably 10 mPa·s or more, even more preferably 20 mPa·s or more, and further preferably 30 mPa·s or more. The liquid composition used preferably has a viscosity at 25° C. of 3,000 mPa·s or less, more preferably 2,000 mPa·s or less, even more preferably 1,500 mPa·s or less, further preferably 1,000 mPa·s or less, and furthermore preferably 800 mPa·s. The liquid composition preferably has a viscosity at 25° C. of 5 mPa·s or more and 3,000 mPa·s or less, more preferably 5 mPa·s or more and 2,000 mPa·s or less, even more preferably 10 mPa·s or more and 1,500 mPa·s or less, further preferably 20 mPa·s or more and 1,000 mPa·s or less, and furthermore preferably 30 mPa·s or more and 800 mPa·s or less. By using a liquid composition having a viscosity within the range, a porous film, especially a porous film formed of deposited fibers can be successfully formed by the electrostatic spraying method. The formation of a porous film is advantageous in view of, e.g., following performance to skin and prevention of humid skin. The viscosity of a liquid composition is determined using an E-type viscometer at 25° C. As the E-type viscometer, for example, an E-type viscometer manufactured by Tokyo Keiki can be used. The measurement is performed at 25° C. with a cone plate rotor No. 43, and the rotation rate is appropriately selected depending on a viscosity: 5 rpm for a viscosity of 500 mPa·s or more; 10 rpm for a viscosity of not less than 150 mPa·s and less than 500 mPa·s; and 20 rpm for a viscosity of less than 250 mPa·s.

In the liquid composition, the ratio of the conductivity Y (µS/cm) to the viscosity X (mPa·s) at 25° C., Y/X, is preferably 0.1 or more, more preferably 0.2 or more, and even more preferably 0.3 or more and is preferably 3.3 or less, more preferably 3 or less, even more preferably 2.5 or less, and further preferably 2 or less, in view of stable formation of a fibrous film and an improvement in adhesion of a film. Specifically, the ratio of the conductivity Y (µS/cm) to the viscosity X (mPa·s) at 25° C., Y/X, is preferably 0.1 or more and 3.3 or less, more preferably 0.2 or more and 3 or less, and even more preferably 0.3 or more and 2.5 or less.

The liquid composition is sprayed by the electrostatic spraying method directly on an application site of human skin as an object. The electrostatic spraying method includes the step of electrostatically spraying a liquid composition on the skin surface using an electrostatic spray device. FIG. 1 is a schematic view showing the configuration of an electrostatic spray device suitably used in the present invention. An electrostatic spray device 10 shown in the figure includes a low-voltage power supply 11. The low-voltage power supply 11 can generate voltages at several volts to ten-odd volts. In order to improve the portability of the electrostatic spray device 10, the low-voltage power supply 11 preferably includes one or more batteries. Using batteries as the low-voltage power supply 11 also provides an advantage such that batteries can be easily replaced as needed. In place of batteries, an AC adapter or the like can also be used as the low-voltage power supply 11.

Figure 2:
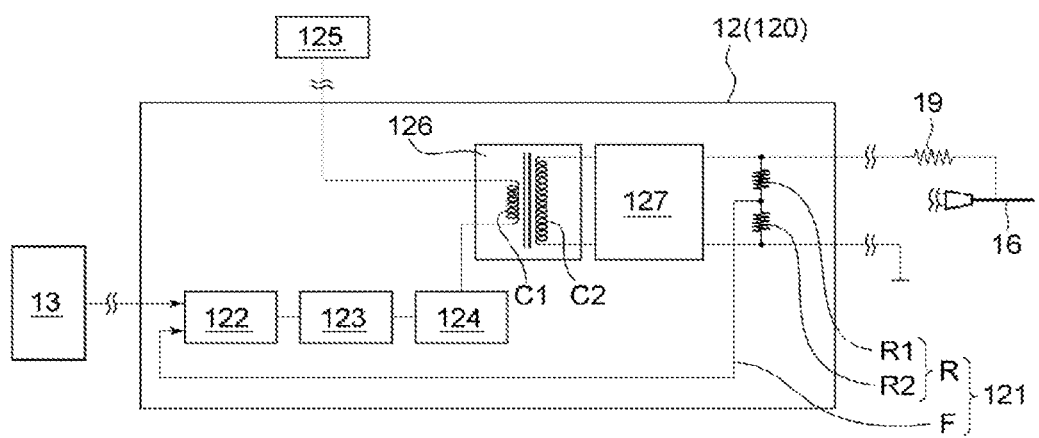
FIG. 2 is a schematic view showing the configuration of an internal circuit in a high-voltage power supply of the electrostatic spray device used in the present invention.

The electrostatic spray device 10 also includes a high-voltage power supply 12. The high-voltage power supply 12 is connected to the low-voltage power supply 11 and includes an electric circuit for boosting the voltage generated by the low-voltage power supply 11 to a high voltage. The booster circuit in FIG. 1 includes, for example, as shown in FIG. 2, a step-up transformer 126 and a voltage multiplier 127 including a capacitor, a semiconductor device, and the like.

The electrostatic spray device 10 further includes an auxiliary circuit 13. The auxiliary circuit 13 is located between the low-voltage power supply 11 and the high-voltage power supply 12 and functions to control the voltage of the low-voltage power supply 11 for stable operation of the high-voltage power supply 12. The auxiliary circuit 13 also functions to control the rotation rate of a motor included in the microgear pump 14 described later. By controlling the rotation rate of the motor, the amount of a liquid composition fed from the liquid composition container 15 described later to the microgear pump 14 is controlled. Between the auxiliary circuit 13 and the low-voltage power supply 11, a switch SW is provided, and on/off control of the switch SW enables operation/stop of the electrostatic spray device 10.

The electrostatic spray device 10 further includes a nozzle 16. The nozzle 16 is made of any of various conductive materials including metal and non-conductive materials including plastic, rubber, and ceramic and has a shape capable of ejecting a liquid composition from the tip thereof. In the nozzle 16, a microspace through which a liquid composition passes is formed along the longitudinal direction of the nozzle 16. In view of preventing the nozzle 16 from clogging, the microspace preferably has a minimum cross-sectional diameter of 100 µm or more and 2,000 µm or less, more preferably 250 µm or more and 1,400 µm or less, and even more preferably 300 µm or more and 1,400 µm or less. From the same viewpoint, the nozzle 16 preferably has a flow path length of 1 mm or more and 25 mm or less, more preferably 1 mm or more and 20 mm or less, even more preferably 5 mm or more and 20 mm or less, and further preferably 5 mm or more and 15 mm or less.

The flow path of the nozzle 16 has at least a tubular shape, and the flow path may branch at a midway point as long as a liquid composition can be ejected. As for the cross section of the flow path, the flow path may have a cylinder shape (tube shape) having a substantially constant cross-sectional area, or the cross-sectional area of a flow path may increase or decrease toward the ejecting direction of a liquid composition.

The nozzle 16 communicates with the microgear pump 14 through a pipeline 17. The pipeline 17 may be conductive or non-conductive. The nozzle 16 is electrically connected to the high-voltage power supply 12. The nozzle 16 and the high-voltage power supply 12 may be electrically connected through an electric conductor (not shown) such as an electrode. This configuration enables high voltage application to the nozzle 16. In this case, the nozzle 16 and the high-voltage power supply 12 are electrically connected through a current-limiting resistor 19, in order to prevent excessive current flow when a human body comes into direct contact with the nozzle 16.

The microgear pump 14 communicating with the nozzle 16 through the pipeline 17 functions as a feeder for feeding a liquid composition stored in the container 15 to the nozzle 16. The microgear pump 14 is activated in response to power supply from the low-voltage power supply 11. The microgear pump 14 is configured to feed a certain amount of the liquid composition to the nozzle 16 in response to control by the auxiliary circuit 13.

The container 15 is connected to the microgear pump 14 through a flexible pipeline 18. In the container 15, a liquid composition is stored. The container 15 is preferably in the form of a replaceable cartridge.

The preferable flow rate of a liquid composition ejected from the nozzle 16 depends on the formulation of a liquid composition and an application site on skin, and the flow rate is preferably 0.1 mL/h or more, more preferably 0.2 mL/h or more, and even more preferably 0.4 mL/h or more. The flow rate of a liquid composition ejected from the nozzle 16 is preferably 100 mL/h or less, more preferably 50 mL/h or less, even more preferably 30 mL/h or less, further preferably 12 mL/h or less, and furthermore preferably 11.5 mL/h or less. More specifically, the flow rate of a liquid composition ejected from the nozzle 16 is preferably 0.1 mL/h or more and 100 mL/h or less, more preferably 0.2 mL/h or more and 50 mL/h or less, even more preferably 0.4 mL/h or more and 30 mL/h or less, further preferably 0.4 mL/h or more and 12 mL/h or less, and furthermore preferably 0.4 mL/h or more and 11.5 mL/h or less. By ejecting a liquid composition at such a flow rate, the adhesion of a film to skin can be improved.

The voltage applied by the high-voltage power supply 12 to the nozzle 16 is preferably 5 kV or more, more preferably 9 kV or more, and even more preferably 10 kV or more in order to maintain the ejection flow rate of a liquid composition in the electrostatic spraying step. The voltage applied to the nozzle 16 is preferably 50 kV or less and more preferably 30 kV or less. More specifically, the voltage applied to the nozzle 16 is preferably 5 kV or more and 50 kV or less, more preferably 9 kV or more and 30 kV or less, and even more preferably 10 kV or more and 30 kV or less. The voltage applied to the nozzle 16 can be appropriately set according to the formulation of a liquid composition and an intended ejecting rate of a liquid composition, and a higher voltage is preferably applied as the flow rate increases. The range of the voltage applied to the nozzle 16 is an absolute value, and the applied voltage may be a positive voltage or a negative voltage referenced to grounding.

When the liquid composition contains the component (c), the ejecting rate (flow rate) of a liquid composition from the nozzle 16 and the voltage applied to the nozzle 16 preferably satisfy a particular relation in view of successful electrostatic spraying and a further improvement in adhesion of a film to skin or the like. Specifically, the ratio of the ejecting rate (flow rate:mL/h) of a liquid composition to the voltage (kV) applied to the nozzle 16, flow rate/voltage, is preferably 0.8 or less and more preferably 0.6 or less, and is preferably 0.06 or more and more preferably 0.1 or more. More specifically, the ratio of the flow rate of a liquid composition to the voltage applied to the nozzle 16, flow rate/voltage, is preferably 0.06 or more and 0.8 or less, more preferably 0.06 or more and 0.6 or less, and even more preferably 0.1 or more and 0.6 or less.

In view of satisfying both the handling properties of the electrostatic spray device 10 and satisfactory ejection of a liquid composition, the container 15 preferably has a volume of 1 mL or more, more preferably 1.5 mL or more, and even more preferably 3 mL or more and is preferably 25 mL or less, more preferably 20 mL or less, and even more preferably 15 mL or less. Specifically, the container 15 preferably has a volume of 1 mL or more and 25 mL or less, more preferably 1.5 mL or more and 20 mL or less, and even more preferably 3 mL or more and 15 mL or less. The container 15 having a volume within such a range also has an advantage that such a compact container can be easily replaced when the container 15 is a replaceable cartridge.

FIG. 2 is a schematic view showing the internal configuration in the high-voltage power supply 12 of the electrostatic spray device 10 used in the present invention. As shown in FIG. 2, the high-voltage power supply 12 preferably includes a voltage stabilizer 120 therein in view of stabilizing the voltage applied from the high-voltage power supply 12 to the nozzle 16 irrespective of conditions of use of the electrostatic spray device 10 and an ambient environment. The voltage stabilizer 120 includes a voltage detector 121, a comparator 122, and a voltage controller 123. The voltage detector 121 includes a voltage dividing resistor circuit R and a voltage feedback circuit F provided on a circuit including the voltage dividing resistor circuit R and is electrically connected to the comparator 122 through the voltage feedback circuit F. The schematic view in FIG. 2 shows the voltage dividing resistor circuit R in which two resistors R1, R2 are connected in series between the nozzle and the grounding. In the schematic view, a resistor in which the resistor R1 has a higher resistance value than the resistance value of the resistor R2 is used, and a high voltage applied to the nozzle 16 is divided between the resistor R1 and the resistor R2. The voltage feedback circuit F is provided between the resistor R1 and the resistor R2 such that the voltage between the resistor R2 and the grounding can be measured. Since the resistor R2 has a lower resistance value than the resistance value of the resistor R1, the voltage across the resistor R2 is lower than the voltage across the resistor R1. A signal according to the voltage across the resistor R2 is output as the voltage applied to the nozzle through the voltage feedback circuit F provided between the resistor R1 and the resistor R2 to the comparator 122. The voltage feedback circuit F may include other devices such as a capacitor therein as needed and may be connected to an electric circuit other than the comparator 122. The grounding is not specifically limited as long as the grounding has a potential difference as compared with the voltage of the nozzle 16, and may be a human body, for example.

The comparator 122 receives the signal according to the voltage applied to the nozzle through the voltage feedback circuit F, and detects the signal as the voltage applied to the nozzle 16. At the same time, the comparator 122 also detects, as a reference voltage, the voltage applied to the high-voltage power supply 12 through the auxiliary circuit 13. The comparator 122 compares the voltage applied to the nozzle 16 to the reference voltage to determine the difference therebetween and outputs the difference analysis result as a signal to the voltage controller 123 electrically connected to the comparator 122. If the difference between the voltage applied to the nozzle 16 and the reference voltage is within a predetermined range, a stationary signal is output to the voltage controller 123. If the difference between the voltage applied to the nozzle 16 and the reference voltage exceeds a predetermined range, a control signal according to the determined voltage difference is output to the voltage controller 123.

The voltage controller 123 is provided between the comparator 122 and an oscillation circuit 124 and is electrically connected thereto. The voltage controller 123 controls the oscillation voltage of the oscillation circuit 124 according to the stationary signal or the control signal input from the comparator 122, thereby controlling the voltage applied by the high-voltage power supply 12 to the nozzle 16. The voltage controller 123 analyzes the stationary signal or the control signal output from the comparator 122 and appropriately changes the oscillation voltage output from the oscillation circuit 124 on the basis of the analysis result. If receiving the stationary signal from the comparator 122, the voltage controller 123 controls the oscillation voltage of the oscillation circuit 124 such that the oscillation voltage maintains a certain voltage. In contrast, if receiving the control signal from the comparator 122, the voltage controller 123 controls the oscillation voltage of the oscillation circuit 124 such that the oscillation voltage reduces the difference between the voltage applied to the nozzle and the reference voltage to maintain a certain voltage.

The oscillation circuit 124 converts the voltage supplied from a direct-current power supply 125 into an alternating current signal according to a signal output from the voltage controller 123, generating an alternating voltage. As the oscillation circuit 124, any known circuit can be used. The oscillation circuit 124 is electrically connected to the direct-current power supply 125 and converts a constant voltage supplied from the direct-current power supply 125 into an intermittent voltage waveform such as a rectangular wave, generating an alternating voltage. The oscillation circuit 124 changes an alternating voltage generated from the oscillation circuit 124 depending on a change in output signal of the voltage controller 123 that is connected to the oscillation circuit 124, and according to the change, also changes the alternating voltage generated in the step-up transformer 126 and the voltage multiplier 127 described later. In FIG. 2, the direct-current power supply 125 is provided outside the high-voltage power supply 12 but may be provided in the high-voltage power supply 12.

Specifically, the step-up transformer 126 includes a primary coil C1 to which the alternating voltage output from the oscillation circuit 124 is applied and a secondary coil C2 that is electromagnetically induced by the alternating voltage applied to the primary coil C1.

To the primary coil C1 of the step-up transformer 126, the oscillation circuit 124 and the direct-current power supply 125 are electrically connected. A voltage supplied from the direct-current power supply is converted by the oscillation circuit 124 into an alternating voltage, and the converted alternating voltage is applied to the primary coil C1. Depending on a change in output signal of the voltage controller 123, the alternating voltage generated by the oscillation circuit 124 is changed, and the voltage applied to the primary coil C1 of the step-up transformer 126 is also changed. As the voltage applied to the primary coil C1 of the step-up transformer 126 varies, the voltage generated in the secondary coil C2 of the step-up transformer 126 varies accordingly. In the circuit diagram shown in FIG. 2, the secondary coil C2 has a larger number of turns than the number of turns of the primary coil C1, and thus the voltage generated in the secondary coil C2 is larger than the voltage applied to the primary coil C1.

The voltage multiplier 127 is a circuit that is connected to the secondary coil C2 of the step-up transformer 126 and further boosts the voltage generated in the secondary coil C2 to voltages at several kilovolts to ten-odd kilovolts, which enable electrostatic spraying of a liquid composition used in the present invention. The voltage multiplier 127 includes, for example, a Cockcroft-Walton circuit including a capacitor, a diode, and the like. The alternating voltage applied to the voltage multiplier 127 is so controlled by a stationary signal or a control signal output from the voltage controller 123 through the oscillation circuit 124 and the step-up transformer 126 as to give a certain voltage.

With the voltage stabilizer 120 having the above configuration in the high-voltage power supply 12, the voltage applied from the high-voltage power supply 12 to the nozzle 16 can be controlled within a certain range, and the electrostatic spraying method thus can be stably performed irrespective of conditions of the ambient environment and use.

The electrostatic spray device 10 preferably further includes a current limiter 30 at the downstream side of the high-voltage power supply 12 in view of preventing an excessive current flow through the electrostatic spray device 10 when a conductive body comes into direct contact with the nozzle 16. The current limiter 30 stops high voltage generation in the high-voltage power supply 12 when a current exceeding a predetermined threshold flows through the electrostatic spray device 10. The predetermined threshold is preferably set at 2 mA or more, more preferably 1 mA or more, and even more preferably 0.1 mA or more.

Figure 3:
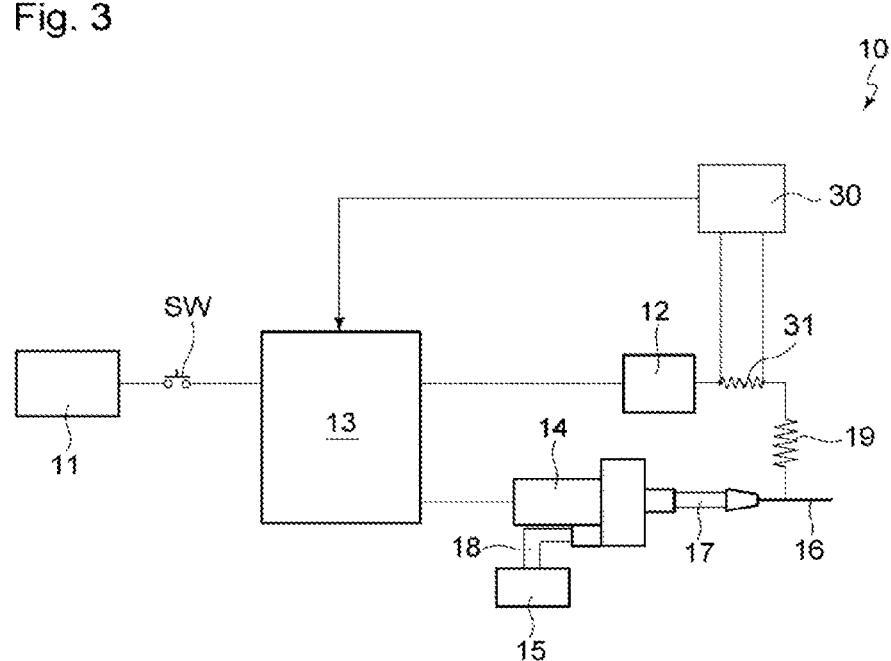
FIG. 3 is a schematic view showing another configuration of the electrostatic spray device used in the present invention.

FIG. 3 is a schematic view showing the configuration of an electrostatic spray device 10 including the current limiter 30. The current limiter 30 is electrically connected to both ends of a current-measuring resistor 31 connected between a high-voltage power supply 12 and a current-limiting resistor 19 in series. As the current limiter 30, for example, a known device such as an isolation amplifier can be used. The current limiter 30 measures the current flowing through the current-measuring resistor 31. If detecting a current exceeding a predetermined threshold, the current limiter outputs a current-limiting signal to an auxiliary circuit 13 that is electrically connected to the current limiter 30. When the current-limiting signal is input to the auxiliary circuit 13, the auxiliary circuit 13 stops high voltage generation in the high-voltage power supply 12, and accordingly, high voltage application to a nozzle 16 is stopped. In addition, the auxiliary circuit 13 to which the current-limiting signal is input stops the movement of a microgear pump 14, and accordingly, the feed of a liquid composition from a liquid composition container 15 to the microgear pump 14 is stopped.

Figure 4:
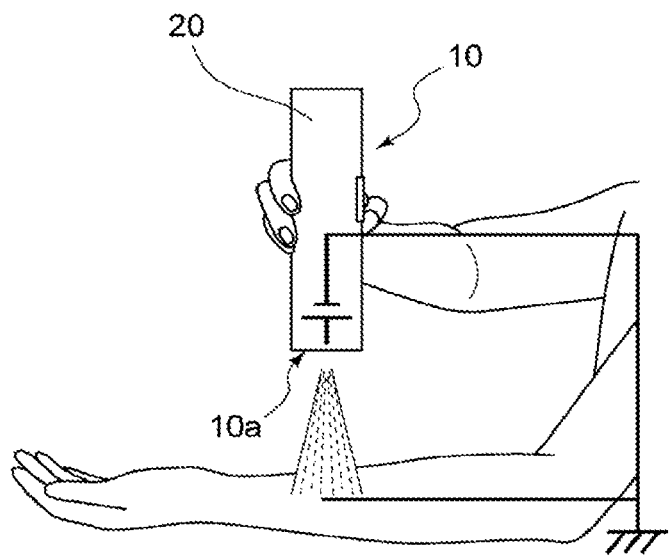
FIG. 4 is a schematic view showing a state in which an electrostatic spray device is used to perform an electrostatic spraying method.

The electrostatic spray device 10 having the above configuration can be used as shown in FIG. 4, for example. FIG. 4 shows a hand-held electrostatic spray device 10 having dimensions that allow a user to hold the device with a single hand. The electrostatic spray device 10 shown in the figure stores all the members in the configuration view shown in FIG. 1 or FIG. 3 in a cylindrical housing 20. The housing 20 shown in FIG. 4 has a cylindrical shape, but a housing 20 may have any shape as long as the housing has dimensions that allow a user to hold the device with a single hand and also allow all the constituent members shown in FIG. 1 or FIG. 3 to be stored. The shape may be of a tubular shape such as an elliptical tube or a regular prism. For the "dimensions that allow a user to hold a device with a single hand", the housing 20 containing the electrostatic spray device 10 preferably has a weight of 2 kg or less, the housing 20 preferably has a maximum length of 40 cm or less in the longitudinal direction, and the housing 20 preferably has a volume of 3,000 $cm^3$ or less. The housing 20 has a nozzle (not shown) at one end 10a in the longitudinal direction. The nozzle is so provided on the housing 20 as to form a convex toward skin while the ejection direction of a liquid composition is coincident with the longitudinal direction of the housing 20. When a nozzle tip is provided to form a convex in the longitudinal direction of the housing 20 toward skin, a liquid composition is unlikely to adhere to the housing, and a film can be stably formed.

When the electrostatic spray device 10 is operated, a user, i.e., a person forming a film on an application site thereof by electrostatic spraying holds the apparatus 10 with the hand thereof and directs the one end 10a of the apparatus 10 to which the nozzle (not shown) is provided to the application site where electrostatic spraying is to be performed. FIG. 4 shows the state in which the one end 10a of the electrostatic spray device 10 is directed to the inner face of a forearm of a user. In this condition, the apparatus 10 is switched on to perform the electrostatic spraying method. When the apparatus 10 is powered, an electric field is formed between the nozzle and the skin. In the embodiment shown in FIG. 4, a positive high voltage is applied to the nozzle, and the skin functions as a negative electrode. When an electric field is formed between the nozzle and the skin, a liquid composition at the nozzle tip is polarized by electrostatic induction to form a cone-shaped tip, and liquid drops of the charged liquid composition are ejected from the cone tip along the electric field into the air toward the skin. When the component (a) as a solvent evaporates from the charged liquid composition ejected into the space, the surface of the liquid composition has an excess charge density. By Coulomb repulsion, the liquid composition spreads in the space while miniaturized repeatedly, and reaches the skin. In this case, by appropriately adjusting the viscosity of the liquid composition, the sprayed composition in a liquid drop state can reach the application site. Alternatively, fibers can be deposited on an application site in the following manner: during ejection into the space, a volatile substance as the solvent is volatilized from liquid drops to solidify a polymer capable of forming a film as the solute; concurrently with this, the polymer is formed into fibers while the fibers are extended and deformed by a potential difference, and the fibers are deposited on the application site. For example, a liquid composition having a higher viscosity is likely to be deposited in a fiber shape on an application site. Accordingly, a porous film formed of deposited fibers is formed on the surface of an application site. A porous film formed of deposited fibers can also be formed by adjusting the distance between the nozzle and skin or the voltage applied to the nozzle.

During performing the electrostatic spraying method, a high potential difference is formed between the nozzle and skin. However, the impedance is very large, and thus an extremely small current flows through a human body. For example, the inventors of the present invention have ascertained that the current flowing through a human body during performing the electrostatic spraying method is several digits smaller than the current flowing through a human body by static electricity generated in a normal life.

When deposited fibers are formed by the electrostatic spraying method, the fibers preferably have a thickness of 10 nm or more and more preferably 50 nm or more in terms of circle equivalent diameter. The thickness is preferably 3,000 nm or less and more preferably 1,000 nm or less. The fiber thickness can be determined as follows: fibers are observed under, for example, a scanning electron microscope (SEM) at a magnification of 10,000; in the two-dimensional image, ten fibers are arbitrarily selected except defects (fiber aggregates, fiber intersections, and liquid drops); and a line orthogonal to the longitudinal direction of each fiber is drawn; and the thickness of the fiber is measured directly.

Each fiber is a continuous fiber with unlimited length in production principle but preferably has a length at least 100 times larger than the thickness of the fiber. Herein, a fiber having a length at least 100 times larger than the thickness of the fiber is defined as a "continuous fiber". The film produced by the electrostatic spraying method is preferably a discontinuous porous film formed of deposited continuous fibers. The film in such a form can be handled as a single aggregate sheet, and advantageously, the film also has very soft characteristics so that the film is unlikely to fragment even when a shear force is applied thereto and has an excellent following performance to body movement. The film has another advantage of excellent diffusion properties of sweat from skin. The film also has an advantage of easy release of the film. In contrast, a continuous film without pores is difficult to release, and has very poor diffusion properties of sweat so that the film is likely to cause humid skin.

The liquid composition in a fibrous form reaches an application site while maintaining a charged state. As described above, the skin is also charged, and thus the fibers come into close contact with the application site by static electricity. The skin surface has a fine unevenness including skin texture, and thus the fibers come into closer contact with the surface of an application site due to the anchor effect of the unevenness. After the electrostatic spraying is completed as above, the electrostatic spray device 10 is powered off. Accordingly, the electric field between the nozzle and the skin disappears, and the charge on the skin surface is fixed. As a result, the adhesion of the film is further exhibited.

As described above, a liquid composition in a charged state is sprayed from the nozzle tip of the electrostatic spray device into the air (into the atmosphere). When the ambient humidity is high during electrostatic spraying, charges leak due to water in the atmosphere, and a lower voltage than the set value is applied to the nozzle in practice. Accordingly, the liquid composition may be charged at a lower degree and may be insufficiently sprayed. In the techniques disclosed in Patent Literatures 1 and 2, specifically, a composition is ejected, and liquid drops are deposited to form a film; in contrast, in the present invention, continuous fibers are formed by Coulomb repulsion of the liquid composition, and the fibers are deposited to form a film. Hence, if the voltage applied to the nozzle and charges of the liquid composition are reduced in the present invention, the quality of the formed film may be affected. When the liquid composition contains the component (c), the electrostatic spraying can be unlikely to be affected by humidity.

When containing the component (c), the liquid composition of the present invention allows a film to be formed to support water while suppressing the effect of humidity on spraying. Specifically, when the liquid composition contains about 0.2% by mass or more of the component (c) and has a mass ratio of the component (b) to the component (c), b/c, of 0.4 or more, the adhesion between skin and a film is improved, and the film is likely to be transparent, resulting in a more natural appearance. The adhesion is further improved by performing the liquid agent-applying step described later before or after the electrostatic spraying step.

In the industrial production where the environmental conditions for the film production including temperature and humidity are controlled, the production environment varies in a small range. In contrast, the temperature and humidity of the environment where the hand-held electrostatic spray device of the embodiment is used is likely to vary, and accordingly a film is difficult to be stably formed, which is a problem specific to hand-held devices. A liquid composition containing the component (d) in addition to the component (c) has a higher conductivity, and accordingly the liquid composition can be stably sprayed by the electrostatic spray device of the present invention even when the environmental conditions for the film production varies. Hence, a film having high adhesion to skin can be formed.

Hereinbefore, the porous film formed of deposited fibers has been described as an exemplary film, but the film form is not limited to this. A continuous film without pores may be formed, or a porous film not in the form of deposited fibers, for example, a porous film obtained by forming a plurality of through-holes irregularly or regularly formed in a continuous film, that is, a discontinuous film may be formed. As described above, by controlling the viscosity of a liquid composition, the distance between the nozzle and skin, the voltage applied to the nozzle, or other conditions, a film having an intended form can be formed.

The distance between the nozzle and skin depends on the voltage applied to the nozzle but is preferably 10 mm or more, more preferably 20 mm or more, even more preferably 40 mm or more, and further preferably 60 mm or more from the viewpoint of successful film formation. The distance between the nozzle and skin is preferably 160 mm or less, more preferably 150 mm or less, and even more preferably 120 mm or less. More specifically, the distance between the nozzle and skin is preferably 10 mm or more and 160 mm or less, more preferably 20 mm or more and 150 mm or less, even more preferably 40 mm or more and 150 mm or less, further preferably 40 mm or more and 120 mm or less, and furthermore preferably 60 mm or more and 120 mm or less. The distance between the nozzle and skin can be determined, for example, by using a common non-contact sensor.

Whether or not the film formed by the electrostatic spraying method is porous, the film preferably has a basis weight of 0.05 g/m² or more, more preferably 0.1 g/m² or more, and even more preferably 1 g/m² or more, relative to 1 m² of skin. The basis weight is preferably 50 g/m² or less, more preferably 40 g/m² or less, even more preferably 30 g/m² or less, further preferably 25 g/m² or less, and furthermore preferably 20 g/m² or less. For example, the film preferably has a basis weight of 0.05 g/m² or more and 50 g/m² or less, more preferably 0.1 g/m² or more and 40 g/m² or less, even more preferably 0.1 g/m² or more and 30 g/m² or less, further preferably 0.1 g/m² or more and 25 g/m² or less, and furthermore preferably 1 g/m² or more and 20 g/m² or less, relative to 1 m² of skin. By setting the film basis weight within the above range, peeling off of the film due to an excess film thickness can be effectively suppressed.

Whether or not the film formed by the electrostatic spraying method is porous, the electrostatic spraying time in the electrostatic spraying method depends on the mixing ratios of components of a liquid composition and the voltage applied to the nozzle but is preferably 5 seconds or more and more preferably 10 seconds or more for 10 cm² of skin in view of effective suppression of peeling off of the film. The electrostatic spraying time in the electrostatic spraying method is preferably 120 seconds or less and more preferably 60 seconds or less. Specifically, the electrostatic spraying time in the electrostatic spraying method is preferably 5 seconds or more and 120 seconds or less and more preferably 10 seconds or more and 60 seconds or less.

The electrostatic spraying step of electrostatically spraying a liquid composition directly on skin means a step of performing electrostatic spraying directly on skin to form a film on the skin. The electrostatic spraying step differs from a series of the steps of electrostatically spraying a liquid composition on a site other than skin to form a sheet formed of fibers and applying or attaching the sheet onto skin.

In the present invention, either before or after the electrostatic spraying step of forming a film by the electrostatic spraying method or both before and after the electrostatic spraying step, the step of applying a cosmetic containing a powder onto the skin or the film may be further included. By performing the cosmetic-applying step before and/or after the electrostatic spraying step of forming a porous film formed of deposited fibers, color migration or adhesion of a cosmetic to clothes or the like can be suppressed even when the site of the skin or the film coated with the cosmetic containing a powder (hereinafter, the site is also called "cosmetic-applied site") is rubbed with clothes or the like. In contrast, the techniques described above in Background Art, i.e., the techniques disclosed in Patent Literatures 1 and 2 merely disclose the formation of a foundation film directly on the skin surface by the electrostatic spraying method but disclose no process of protecting the formed foundation film.

In the present invention, it is particularly preferred to apply a liquid composition onto a cosmetic-applied site to form a film, thereby covering the cosmetic surface to protect the cosmetic. In other words, the electrostatic spraying step of forming a film by the electrostatic spraying method described above is preferably performed after the cosmetic-applying step. In addition, the film is preferably formed over the whole region of a cosmetic-applied site in view of surely preventing color migration or adhesion of the cosmetic to a substance such as clothes coming into contact with skin and also in view of holding the cosmetic on the skin. In some cases, the film may be formed only in a part of the cosmetic-applied site. Alternatively, the film may be formed over both the cosmetic-applied site and the site without a cosmetic.

Examples of the cosmetic include preparations for external use exhibiting favorable effects on skin, such as a makeup cosmetic, a UV cosmetic, and a beauty essence. Examples of the makeup cosmetic include a base makeup cosmetic, a lip cosmetic, a makeup base, a BB cream, and a CC cream. Examples of the base makeup cosmetic include a foundation, a concealer, and a face powder. The base makeup cosmetic contains a color pigment, an extender pigment, or the like, and it is no essential difference which form the base makeup cosmetic is in, a liquid form, a gel form, an emulsion form, or a solid form.

In the cosmetic, the content of the powder varies according to purposes but is preferably 0.1% by mass or more and is preferably 100% by mass or less and more preferably 95% by mass or less in view of an improvement in adhesion between skin and the film formed by the electrostatic spraying method. In the present invention, the powder is preferably a color pigment or a pearl pigment in view of providing favorable effects on skin by the makeup cosmetic, the UV cosmetic, the beauty essence, or the like. In the present invention, the color pigment encompasses colored pigments and white pigments. From the same viewpoint, the color pigment preferably has an average particle diameter of 0.1 μm or more and more preferably more than 0.1 μm and is preferably 20 μm or less and more preferably 15 μm or less. The average particle diameter is a number average particle diameter determined with a laser diffraction/scattering particle size distribution analyzer LA-910 (manufactured by Horiba, Ltd.).

The color pigment and the extender pigment contained in the base makeup cosmetic may be any pigment used in common cosmetics. Examples include powders of inorganic substances such as silicic acid, silicic anhydride, magnesium silicate, talc, sericite, mica, kaolin, colcothar, clay, bentonite, isinglass, titanium-coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine, chromium oxide, chromium hydroxide, calamine, carbon black, boron nitride, and composites thereof; powders of organic substances such as polyamide, nylon, polyester, polypropylene, polystyrene, polyurethane, a vinyl resin, a urea resin, a phenol resin, a fluorine resin, a silicon resin, an acrylic resin, a melamine resin, an epoxy resin, a polycarbonate resin, a divinylbenzene/styrene copolymer, silk powder, cellulose, a metal long-chain alkyl phosphate, an N-mono-long-chain alkyl acyl basic amino acid, and composites thereof; and composite powders of such an inorganic powder and such an organic powder. These extender pigments and color pigments have colors or no color (for example, white or essentially transparent) and can give the composition or skin at least one of the effects including coloring, light diffraction, oil absorption, translucency, opacity, gloss, an appearance without gloss, and smoothness.

The color pigment and the extender pigment contained in the cosmetic in the present invention may be any pigment used in common cosmetics. Examples include powders of inorganic substances such as silicic acid, silicic anhydride, magnesium silicate, talc, sericite, mica, kaolin, colcothar, clay, bentonite, isinglass, titanium-coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine, chromium oxide, chromium hydroxide, calamine, carbon black, boron nitride, and composites thereof; powders of organic substances such as polyamide, nylon, polyester, polypropylene, polystyrene, polyurethane, a vinyl resin, a urea resin, a phenol resin, a fluorine resin, a silicon resin, an acrylic resin, a melamine resin, an epoxy resin, a polycarbonate resin, a divinylbenzene/styrene copolymer, silk powder, cellulose, a metal long-chain alkyl phosphate, an N-mono-long-chain alkyl acyl basic amino acid, and composites thereof; and composite powders of such an inorganic powder and such an organic powder. These extender pigments and color pigments have colors or no color (for example, white or essentially transparent) and can give the composition or skin at least one of the effects including coloring, light diffraction, oil absorption, translucency, opacity, gloss, an appearance without gloss, and smoothness.

In view of effectively preventing adhesion to clothes, the cosmetic preferably contains a color pigment or a pearl pigment. Examples of the color pigment include inorganic pigments such as titanium oxide, zinc oxide, yellow iron oxide, red iron oxide, black iron oxide, carbon black, ultramarine, iron blue, blue titanium oxide, black titanium oxide, chromium oxide, chromium hydroxide, and a titanium/titanium oxide sinter; organic pigments such as Red No. 201, Red No. 202, Red No. 226, Yellow No. 401, and Blue No. 404; lake pigments such as Red No. 104, Red No. 230, Yellow No. 4, Yellow No. 5, and Blue No. 1; and a pigment prepared by coating an organic pigment with a polymer such as a polymethacrylic acid ester. Examples of the pearl pigment include powders of inorganic substances such as mica titanium, colcothar-coated mica, bismuth oxychloride, titanium oxide-coated bismuth oxychloride, iron oxide-coated mica titanium, organic pigment-coated mica titanium, silicic acid/titanium-treated mica, titanium oxide-coated talc, silicon dioxide/colcothar-treated aluminum, and titanium oxide-coated glass powder; and flaky aluminum having a surface coated with an organic resin such as polyethylene terephthalate. These color pigments, extender pigments, and pearl pigments may be surface-treated with a fluorine compound or a silicone compound in view of endurance against sweat or sebum, for example.

In view of effectively preventing adhesion to clothes, the cosmetic preferably contains a color pigment or a pearl pigment. Examples of the color pigment include inorganic white pigments such as titanium oxide and zinc oxide; inorganic color pigments such as yellow iron oxide, red iron oxide, black iron oxide, carbon black, ultramarine, iron blue, blue titanium oxide, black titanium oxide, chromium oxide, chromium hydroxide, and a titanium/titanium oxide sinter; organic pigments such as Red No. 201, Red No. 202, Red No. 226, Yellow No. 401, and Blue No. 404; lake pigments such as Red No. 104, Red No. 230, Yellow No. 4, Yellow No. 5, and Blue No. 1; and a pigment prepared by coating an organic pigment with a polymer such as a polymethacrylic acid ester. Examples of the pearl pigment include powders of inorganic substances such as mica titanium, colcothar-coated (titanium oxide/aluminum hydroxide) mixture, colcothar-coated mica, bismuth oxychloride, titanium oxide-coated bismuth oxychloride, iron oxide-coated mica titanium, organic pigment-coated mica titanium, silicic acid/titanium-treated mica, titanium oxide-coated talc, silicon dioxide/colcothar-treated aluminum, and titanium oxide-coated glass powder; and flaky aluminum having a surface coated with an organic resin such as polyethylene tereph- thalate and a titanium oxide-yellow iron oxide-colcothar/lauryl methacrylate-dimethacrylic acid EG copolymer mixture.

Specifically, a cosmetic containing, as a color pigment, at least titanium oxide, yellow iron oxide, red iron oxide, or black iron oxide has an excellent makeup effect and can be effectively prevented from adhering to clothes. These color pigments and pearl pigments may be hydrophobically treated in view of endurance against sweat, sebum and the like. The hydrophobic treatment is preferably surface treatment such as fluorine compound treatment, silicone compound treatment, alkyl treatment, alkylsilane treatment, metallic soap treatment, water-soluble polymer treatment, amino acid treatment, N-acylamino acid treatment, lecithin treatment, organic titanate treatment, polyol treatment, acrylic resin treatment, methacrylic resin treatment, and urethane resin treatment. Specifically, a pigment surface-treated with a fluorine compound or a silicone compound is more preferred.

The color pigments and the pearl pigments may be used singly or in combination of two or more of them. In view of effectively preventing adhesion to clothes, the content in the total composition is preferably 0.1% by mass or more, more preferably 0.5% by mass or more, and even more preferably 1% by mass or more and is preferably 40% by mass or less, more preferably 30% by mass or less, and even more preferably 25% by mass or less. The content of the color pigment or the pearl pigment is preferably 0.1 to 40% by mass, more preferably 0.5 to 30% by mass, and even more preferably 1 to 25% by mass in the total composition.

The makeup cosmetic may further contain an oil that is liquid at 25° C., a wax that is solid at 25° C., or the like, in addition to the powder such as a color pigment and an extender pigment. The makeup cosmetic may further contain common components such as a thickener, a film forming agent, a surfactant, a sugar, a polyhydric alcohol, a water-soluble polymer, a sequestrant, a lower alcohol, an amino acid, an organic amine, a pH adjuster, a skin conditioner, a vitamin, an antioxidant, a fragrance chemical, and an antiseptic agent appropriately as long as the effects of the invention are not impaired.

The UV cosmetic preferably contains a component having ultraviolet protection ability, such as an ultraviolet absorber and an ultraviolet scattering agent. As the ultraviolet absorber, for example, one or more organic ultraviolet absorbers selected from benzophenone derivatives such as dihydroxybenzophenone, dihydroxydimethoxybenzophenone, hydroxymethoxybenzophenone sulfonate, and dihydroxydimethoxybenzophenone disulfonate and methoxycinnamic acid derivatives such as 2-ethylhexyl methoxycinnamate are preferred, and 2-ethylhexyl methoxycinnamate is more preferred. Examples of the ultraviolet scattering agent include zinc oxide microparticles, titanium oxide microparticles, and silica microparticles having an average particle diameter of 0.1 μm or less. Before or after the application of the cosmetic for the present invention onto skin, a cosmetic other than the cosmetic for the present invention may be applied onto skin.

In the present invention, before, after, or before and after the electrostatic spraying step of forming a film on skin by electrostatic spraying, the step of applying, onto skin or the film, a liquid agent that contains one or more substances selected from water, a polyol that is liquid at 20° C., and an oil that is liquid at 20° C. and differs from the above liquid composition may be performed in place of the above cosmetic-applying step. By performing the liquid agent-applying step, the film formed in the electrostatic spraying step is likely to fit with skin, and thus the film can be in closer contact with the skin and can also be transparent. For example, a level difference is unlikely to be formed between the film edge and skin, and this improves the adhesion between the film and the skin. As a result, the film is unlikely to peel off or be broken, for example. In addition, the color of a makeup cosmetic is unlikely to be hidden, thereby providing a more natural appearance, and the presence of the film can be unlikely to be visualized. When the film is a porous film formed of deposited fibers, which is a more preferred embodiment, the film has a high adhesion to skin despite the high void ratio and is likely to generate a large capillary force. When containing ultrafine fibers, the porous film can easily have a high specific surface area. The liquid agent-applying step can be performed by applying a liquid agent onto skin or a film by electrostatic spraying, but a liquid agent is preferably applied onto skin or a film by a method other than the electrostatic spraying, for example, applied with the hand in view of simpleness.

In particular, by performing the liquid agent-applying step after the electrostatic spraying step of forming a porous film formed of deposited fibers, a moisturizing liquid agent-supporting film is formed in which the liquid agent is supported among the fibers forming the porous film and/or on the fiber surface. This improves the adhesion of the film and maintains or improves visual transparency of the film. When the film is particularly colorless and transparent or colored and transparent, the film is more unlikely to be visualized and thus can have a natural skin appearance. When the film is colored and transparent, transparency of the film is enhanced and thus the film can look like a part of the skin.

For the case where the liquid agent used in the liquid agent-applying step contains water, examples of the liquid agent include a liquid such as water, an aqueous solution, and an aqueous dispersion, a gel thickened by a thickener, a polar oil, an oil solution containing 10% by mass or more of a polar oil, and an emulsion containing a polar oil (O/W emulsions, W/O emulsions).

For the case where the liquid agent used in the liquid agent-applying step contains a polyol that is liquid at 20° C., examples of the polyol include alkylene glycols such as ethylene glycol, propylene glycol, 1,3-propanediol, and 1,3-butanediol; polyalkylene glycols such as diethylene glycol, dipropylene glycol, a polyethylene glycol having a weight average molecular weight of 2,000 or less, and a polypropylene glycol; and glycerols such as glycerol, diglycerol, and triglycerol. Of them, in view of sense of use including smoothness at the time of application, ethylene glycol, propylene glycol, 1,3-butanediol, dipropylene glycol, a polyethylene glycol having a weight average molecular weight of 2,000 or less, glycerol, and diglycerol are preferred; propylene glycol, 1,3-butanediol, and glycerol are more preferred; and propylene glycol and 1,3-butanediol are even more preferred.

For the case where the liquid agent used in the liquid agent-applying step contains an oil that is liquid at 20° C. (hereinafter, the oil is also called "liquid oil"), examples of the oil that is liquid at 20° C. include linear or branched hydrocarbon oils such as liquid paraffin, light isoparaffin, liquid isoparaffin, squalane, and squalene; ester oils such as a monohydric alcohol fatty acid ester, a polyhydric alcohol fatty acid ester, and a triglycerol fatty acid ester; and silicone oils such as dimethylpolysiloxane, dimethylcyclopolysiloxane, methylphenylpolysiloxane, methylhydrogenpolysiloxane, and a higher alcohol-modified organopolysiloxane. Of them, in view of sense of use including smoothness at the time of application, hydrocarbon oils and polar oils such as ester oils and silicone oils are preferred, and hydrocarbon oils and ester oils are more preferred. Liquid oils selected from these oils may be used singly or in combination of two or more of them.

Examples of the hydrocarbon oil include liquid paraffin, squalane, squalene, n-octane, n-heptane, cyclohexane, light isoparaffin, and liquid isoparaffin. In view of sense of use, liquid paraffin and squalane are preferred. In view of close contact of the electrostatically sprayed film with skin, the hydrocarbon oil preferably has a viscosity at 30° C. of 10 mPa·s or more and more preferably 30 mPa·s or more. From the same viewpoint, the total content of isododecane, isohexadecane, and hydrogenated polyisobutene, which have a viscosity at 30° C. of less than 10 mPa·s, in the liquid agent is preferably 10% by mass or less, more preferably 5% by mass or less, even more preferably 1% by mass or less, and further preferably 0.5% by mass or less, or such a component may not be contained.

Similarly, in view of close contact of the electrostatically sprayed film with skin, the ester oil and the silicone oil preferably have a viscosity at 30° C. of 10 mPa·s or more and more preferably 30 mPa·s or more.

The viscosity is determined at 30° C. by using a BM-type viscometer (manufactured by Tokimec, Inc., measurement conditions: with a rotor No. 1, at 60 rpm, for 1 minute).

From the same viewpoint, the total content of the ether oils such as cetyl 1,3-dimethylbutyl ether, dicaprylyl ether, dilauryl ether, and diisostearyl ether in the liquid agent is preferably 10% by mass or less, more preferably 5% by mass or less, and even more preferably 1% by mass or less.

As the liquid oil, a polar oil that is liquid at 20° C. can also be preferably used, and examples include ester oils, plant oils including ester oils (triglycerides), higher alcohols of branched fatty acids or unsaturated fatty acids, antiseptic agents, and silicone oil. These liquid oils may be used singly or in combination of two or more of them.

Examples of the ester oil include esters of a linear or branched fatty acid and a linear or branched alcohol or polyhydric alcohol and triglycerol fatty acid esters (triglycerides). Specific examples include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, trimethylolpropane triisostearate, cetyl 2-ethylhexanoate, 2-ethylhexyl palmitate, diethylhexyl naphthalenedicarboxylate, (C12 to 15)-alkyl benzoates, cetearyl isononanoate, glyceryl tri(caprylate/caprate), butylene glycol (dicaprylate/caprate), glyceryl trilaurate, glyceryl trimyristate, glyceryl tripalmitate, glyceryl triisostearate, glyceryl tri-2-heptylundecanoate, glyceryl tribehenate, tricoconut oil fatty acid glyceride, castor oil fatty acid methyl ester, oleyl oleate, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecy palmitate, 2-hexyldecyl adipate, diisopropyl sebacate, di-2-ethylhexyl succinate, triethyl citrate, 2-ethylhexyl p-methoxycinnamate, and tripropylene glycol dipivalate.

Of them, in view of close contact of the electrostatically sprayed film with skin and excellent feeling at the time of application onto skin, at least one selected from octyldodecyl myristate, myristyl myristate, isocetyl stearate, isocetyl isostearate, cetearyl isononanoate, diisobutyl adipate, di-2-ethylhexyl sebacate, isopropyl myristate, isopropyl palmitate, diisostearyl malate, neopentyl glycol dicaprate, (C12 to 15)-alkyl benzoates, and glyceryl tri(caprylate/caprate) is preferred; at least one selected from isopropyl myristate, isopropyl palmitate, diisostearyl malate, neopentyl glycol dicaprate, (C12 to 15)-alkyl benzoates, and glyceryl tri(caprylate/caprate) is more preferred; and at least one selected from neopentyl glycol dicaprate, (C12 to 15)-alkyl benzoates, and glyceryl tri(caprylate/caprate) is even more preferred.

The triglyceride is preferably a fatty acid triglyceride, which is contained, for example, in olive oil, jojoba oil, macadamia nut oil, meadowfoam oil, castor oil, safflower oil, sunflower oil, avocado oil, canola oil, apricot kernel oil, rice germ oil, or rice bran oil.

Examples of the higher alcohol include liquid higher alcohols having 12 to 20 carbon atoms, and specific examples include isostearyl alcohol and oleyl alcohol.

Examples of the antiseptic agent include phenoxyethanol, methyl p-hydroxybenzoate, ethyl p-aminobenzoate, isobutyl p-hydroxybenzoate, isopropyl p-hydroxybenzoate, ethyl p-hydroxybenzoate, butyl p-hydroxybenzoate, propyl p-hydroxybenzoate, benzyl p-hydroxybenzoate, and ethylhexanediol.

Examples of the silicone oil include dimethylpolysiloxane, dimethylcyclopolysiloxane, methylphenylpolysiloxane, methylhydrogenpolysiloxane, and a higher alcohol-modified organopolysiloxane.

The silicone oil preferably has a dynamic viscosity at 25° C. of 3 $mm^2/s$, more preferably 4 $mm^2/s$, and even more preferably 5 $mm^2/s$ or more and is preferably 30 $mm^2/s$ or less, more preferably 20 $mm^2/s$ or less, and even more preferably 10 $mm^2/s$ or less in view of close contact of the electrostatically sprayed film with skin.

Of them, dimethylpolysiloxane is preferably contained in view of close contact of the electrostatically sprayed film with skin.

The liquid agent preferably contains a liquid oil, and the content of the liquid oil in the liquid agent is preferably 0.1% by mass or more, more preferably 0.5% by mass or more, and even more preferably 5% by mass or more. The content is preferably 100% by mass or less. The content of the liquid oil in the liquid agent is preferably 0.1% by mass or more and 100% by mass or less and more preferably 0.5% by mass or more and 100% by mass or less.

Particularly, when the liquid agent contains a polar oil, the liquid agent preferably contains water with the polar oil in view of an improvement in adhesion of a film to skin, and the total content of water and the polar oil in the liquid agent is preferably 40% by mass or more and 100% by mass or less. The liquid agent may contain a surfactant, a polymer, or a thickener in view of stability, and may contain an oily substance that is solid at 30° C., such as vaseline, cetanol, stearyl alcohol, and ceramide, in view of an improvement in adhesion to skin or in moisturization performance of a film.

Similarly, when the liquid agent contains a polyol, the liquid agent preferably contains water with the polyol in view of an improvement in adhesion of a film to skin, and the total content of water and the polyol in the liquid agent is preferably 40% by mass or more and 100% by mass or less. The liquid agent may contain a surfactant, a polymer, or a thickener in view of stability, and may contain an oily substance that is solid at 30° C., such as vaseline, cetanol, stearyl alcohol, and ceramide, in view of an improvement in adhesion to skin or in moisturization performance of a film.

Even when the liquid agent contains any of water, a polyol that is liquid at 20° C., and a liquid oil, the liquid agent preferably has a viscosity of about 5,000 mPa·s or less at 25° C. in view of an improvement in adhesion between the film formed by the electrostatic spraying method and a cosmetic-applied site. The measurement method of the viscosity of a liquid is as described above.

The content of the color pigment in the liquid agent is preferably less than 0.1% by mass, more preferably 0.05% by mass or less, even more preferably 0.01% by mass or less, and further preferably 0.001% by mass or less in view of an improvement in adhesion between skin and the film formed by the electrostatic spraying method. In the present invention, the color pigment excludes transparent pigments, and a white pigment is included in the color pigment.

To apply a liquid agent containing water, a polyol, or a liquid oil onto skin, various methods can be used. For example, the liquid agent is applied onto skin by dropping, sprinkling, or another method, and then spread. Such steps enable the liquid agent to fit with the skin or a film, forming a thin layer of the liquid agent. The liquid agent-spreading step can be performed by rubbing with the finger(s) of a user or a tool such as an applicator. Although the liquid agent may be simply dropped or sprinkled, the spreading step enables fitting the liquid agent with skin or a film, and the film adhesion can be sufficiently improved. As an alternative method, the liquid agent may be sprayed on skin to form a thin layer of the liquid agent. In this case, spreading is not required additionally, but spreading after spraying is acceptable. When the liquid agent is applied after film formation, a sufficient amount of the liquid agent can be applied onto skin, and a sheet material can be brought into contact with the area with the liquid agent to remove an excess liquid agent.

The amount of the liquid agent applied onto skin is an amount necessary and sufficient for an improvement in adhesion between the skin and a film. When the liquid agent contains a liquid oil, the amount of the liquid agent applied onto skin is an amount such that the basis weight of the liquid oil is preferably 0.1 $g/m^2$ or more and more preferably 0.2 $g/m^2$ or more and is preferably 40 $g/m^2$ or less and more preferably 35 $g/m^2$ or less in view of sufficient adhesion between skin and a film. For example, the amount of the liquid agent applied to skin is an amount such that the basis weight of the liquid oil is preferably 0.1 $g/m^2$ or more and 40 $g/m^2$ or less and more preferably 0.2 $g/m^2$ or more and 35 $g/m^2$ or less.

The amount of the liquid agent applied to skin or a film is preferably 5 $g/m^2$ or more, more preferably 10 $g/m^2$ or more, and even more preferably 15 $g/m^2$ or more and is preferably 50 $g/m^2$ or less and more preferably 45 $g/m^2$ or less in view of an improvement in adhesion between skin and a film and an improvement in transparency.

Before or after the application of the liquid agent onto skin, a cosmetic other than the liquid agent may be applied onto skin.

In the present invention, before, after, or before and after the electrostatic spraying step of forming a film on skin by electrostatic spraying, both the cosmetic-applying step and the liquid agent-applying step may be performed. In this case, the steps may be performed in any order, but it is preferred that after the cosmetic-applying step, the electrostatic spraying step be performed, and that after the electrostatic spraying step, the liquid agent-applying step be performed. By forming a film in this step order, color migration or adhesion of a cosmetic to clothes or the like by rubbing or the like of a cosmetic-applied site can be effectively prevented, and a film formed in the electrostatic spraying step is likely to fit with the cosmetic-applied site. The film can be thus in closer contact with the skin and can also be transparent. A level difference is unlikely to be formed between the film edge and skin, and this improves the adhesion between the film and the skin. As a result, the film is unlikely to peel off or be broken, for example. In addition, the color of a makeup cosmetic is unlikely to be hidden, thereby providing a more natural appearance, and the presence of the film can be unlikely to be visualized.

The method for producing a film as described above is useful as various beauty methods excluding a surgery method, a therapeutic treatment method, or a diagnostic method for human bodies. For example, the method for producing a film of the present invention can be applied to beauty care for skin whitening in an application site, concealment of skin blotches, concealment of skin darkening/shadow, concealment of skin wrinkles, skin shading, protection of skin from ultraviolet light, and skin moisturization. In addition, the method for producing a film of the present invention can also be applied to various processes for skin protection performed personally in home, including protection of various wounds such as abraded wound, cut wound, laceration, and stab wound and prevention of bedsore.

The present invention has been described on the basis of the preferred embodiments thereof, but the present invention is not limited to the above embodiments. For example, in the above embodiment, a person intended to form a film on the skin thereof holds the electrostatic spray device 10 to form an electric field between the conductive nozzle of the apparatus 10 and the skin of the person, but a person intended to form a film on the skin thereof does not need to hold the electrostatic spray device 10 as long as an electric field is formed therebetween.

In consideration of the above embodiments, the present invention further discloses the following methods for producing a film.

<1>

A method for producing a film, the method including the step of electrostatically spraying a liquid composition directly on a surface of skin using an electrostatic spray device to form a film on the skin, in which the electrostatic spray device includes a container capable of storing the liquid composition, a nozzle configured to eject the liquid composition, a power supply configured to apply a voltage to the nozzle, and a voltage stabilizer configured to stabilize the voltage applied by the power supply to the nozzle, and the liquid composition contains component (a) and component (b):

(a) one or more volatile substances selected from alcohols and ketones, and (b) a polymer having film formability.

<2>

The method for producing a film as set forth in clause <1>, in which the voltage stabilizer includes a voltage detector configured to detect the voltage applied to the nozzle, a comparator configured to compare the voltage detected by the voltage detector to a reference voltage to determine a difference therebetween and to output a signal, and a voltage controller configured to control the voltage of the power supply on the basis of the signal output from the comparator.

<3>

The method for producing a film as set forth in clause <1> or <2>, in which the electrostatic spray device further includes a current limiter configured to stop high voltage generation in the power supply when a current of 2 mA or more flows.

<4>

The method for producing a film as set forth in any one of clauses <1> to <3>, in which the liquid composition further contains water as component (c), and the mass ratio of a content of the component (b) to a content of the component (c), b/c, is 0.4 or more and 50 or less.

<5>

The method for producing a film as set forth in any one of clauses <1> to <4>, in which in the electrostatic spraying step, the liquid composition is electrostatically sprayed on skin using the electrostatic spray device to form a porous film formed of deposited fibers.

<6>

The method for producing a film as set forth in any one of clauses <1> to <5>, the method including the electrostatic spraying step and the step of applying, onto skin, a liquid agent that contains one or more substances selected from water, a polyol, and an oil that is liquid at 20° C. and differs from the liquid composition.

<7>

The method for producing a film as set forth in clause <6>, in which in the electrostatic spraying step, a porous film formed of deposited fibers is formed, and then in the liquid agent-applying step, the liquid agent is applied onto the porous film to form a liquid agent-supporting film in which the liquid agent is supported among the fibers forming the porous film and/or on a fiber surface.

<8>

The method for producing a film as set forth in clause <6> or <7>, in which in the liquid agent-applying step, the liquid agent is applied onto the film to maintain transparency of the film.

<9>

The method for producing a film as set forth in any one of clauses <1> to <8>, the method further including the step of applying a cosmetic containing a powder onto a surface of skin, in which after the cosmetic-applying step, the electrostatic spraying step is performed.

<10>

The method for producing a film as set forth in any one of clauses <1> to <9>, in which the electrostatic spray device further includes a housing, and the housing stores the container, the nozzle, the power supply, and the voltage stabilizer and is to be held by a single hand.

<11>

The method for producing a film as set forth in any one of clauses <1> to <10>, in which in the electrostatic spraying step, the power supply applies a voltage of 5 kV or more and 50 kV or less to the nozzle to eject the liquid composition at a flow rate of 0.1 mL/h or more and 100 mL/h or less, to thereby perform electrostatic spraying on the surface of the skin.

<12>

The method for producing a film as set forth in any one of clauses <1> to <11>, in which the liquid composition has a viscosity at 25° C. of 5 mPa·s or more and 3,000 mPa·s or less.

<13>
The method for producing a film as set forth in any one of clauses <1> to <12>, in which the component (b) is at least one selected from the group consisting of pullulan, a partially saponified polyvinyl alcohol, a low-saponified polyvinyl alcohol, polyvinylpyrrolidone, polyethylene oxide, a completely saponified polyvinyl alcohol, a polyvinyl butyral resin, a polymethacrylic acid resin, polyvinylacetal diethylaminoacetate, an oxazoline-modified silicone, a water-soluble polyester, polylactic acid, and zein.

<14>
The method for producing a film as set forth in any one of clauses <1> to <13>, in which the liquid composition contains the component (b) in an amount of 5% by mass or more and 40% by mass or less.

<15>
The method for producing a film as set forth in any one of clauses <1> to <14>, in which the liquid composition contains ethanol as the component (a) and further contains water as component (c),
the component (a) is contained in an amount of 55% by mass or more and 92% by mass or less, and
the mass ratio of the content of the component (a) to the content of the component (c), a/c, is 3.5 or more and 210 or less.

<16>
The method for producing a film as set forth in any one of clauses <1> to <15>, in which the liquid composition contains ethanol as the component (a), and
the mass ratio of the content of the component (b) to the content of the component (a), b/a, is 0.02 or more and 0.7 or less.

<17>
The method for producing a film as set forth in any one of clauses <1> to <16>, in which in the electrostatic spraying step, a distance between the nozzle and the skin is 10 mm or more and 160 mm or less.

<18>
The method for producing a film as set forth in any one of clauses <1> to <17>, in which the liquid composition has a conductivity at 25° C. of 8 µS/cm or more and 260 µS/cm or less.

<19>
The method for producing a film as set forth in any one of clauses <1> to <18>, in which in the electrostatic spraying step, the film has a basis weight of 0.05 g/m² or more and 50 g/m² or less relative to 1 m² of the skin.

<20>
A method for producing a film, including the step of electrostatically spraying a liquid composition directly on a surface of skin using an electrostatic spray device to form a film on the skin, in which
the electrostatic spray device includes
a container capable of storing the liquid composition,
a nozzle configured to eject the liquid composition, and
a power supply configured to apply a voltage to the nozzle,
the liquid composition contains component (a) and component (b):
(a) one or more volatile substances selected from alcohols and ketones, and
(b) a polymer having film formability, and
in the electrostatic spraying step, the power supply applies a voltage of 5 kV or more and 50 kV or less to the nozzle to eject the liquid composition at a flow rate of 0.1 mL/h or more and 100 mL/h or less, to thereby perform electrostatic spraying on the surface of the skin.

<21>
The method for producing a film as set forth in clause <20>, in which the liquid composition has a viscosity at 25° C. of 5 mPa·s or more and 3,000 mPa·s or less.

<22>
The method for producing a film as set forth in clause <20> or <21>, in which the component (b) is at least one selected from the group consisting of pullulan, a partially saponified polyvinyl alcohol, a low-saponified polyvinyl alcohol, polyvinylpyrrolidone, polyethylene oxide, a completely saponified polyvinyl alcohol, a polyvinyl butyral resin, a polymethacrylic acid resin, polyvinylacetal diethylaminoacetate, an oxazoline-modified silicone, a water-soluble polyester, polylactic acid, and zein.

<23>
The method for producing a film as set forth in any one of clauses <20> to <22>, in which the liquid composition contains the component (b) in an amout of 5% by mass or more and 40% by mass or less.

<24>
The method for producing a film as set forth in any one of clauses <20> to <23>, in which the liquid composition further contains water as component (c), and
the mass ratio of the content of the component (b) to the content of the component (c),b/c, is 0.6 or more and 140 or less.

<25>
The method for producing a film as set forth in any one of clauses <20> to <24>, in which in the electrostatic spraying step, a distance between the nozzle and the skin is 10 mm or more and 160 mm or less.

<26>
The method for producing a film as set forth in any one of clauses <20> to <25>, in which the liquid composition has a conductivity at 25° C. of 8 µS/cm or more and 260 µS/cm or less.

<27>
The method for producing a film as set forth in any one of clauses <20> to <26>, in which in the electrostatic spraying step, the film has a basis weight of 0.05 g/m² or more and 50 g/m² or less relative to 1 m² of the skin.

<28>
The method for producing a film as set forth in any one of clauses <20> to <27>, in which in the electrostatic spraying step, the liquid composition is electrostatically sprayed on skin to form a porous film formed of deposited fibers.

<29>
The method for producing a film as set forth in any one of clauses <20> to <28>, including the electrostatic spraying step and the step of applying, onto skin, a liquid agent that contains one or more substances selected from water, a polyol, and an oil that is liquid at 20° C., and differs from the liquid composition.

<30>
The method for producing a film as set forth in clause <29>, in which in the electrostatic spraying step, a porous film formed of deposited fibers is formed, and then
in the liquid agent-applying step, the liquid agent is applied onto the porous film to form a liquid agent-supporting film in which the liquid agent is supported among the fibers forming the porous film and/or on a fiber surface.

<31>
The method for producing a film as set forth in clause <29> or <30>, in which in the liquid agent-applying step, the liquid agent is applied onto the film to maintain transparency.

<32>

The method for producing a film as set forth in any one of clauses <29> to <31>, the method further including the step of applying a cosmetic containing a powder onto a surface of skin, in which after the cosmetic-applying step, the electrostatic spraying step is performed.

<33>

The method for producing a film as set forth in any one of clauses <20> to <32>, in which the electrostatic spray device further includes a housing, and the housing stores the container, the nozzle, and the power supply and is to be held by a single hand.

<34>

The method for producing a film as set forth in any one of clauses <1> to <33>, in which the container has a volume of 1 mL or more and 20 mL or less.

<35>

The method for producing a film as set forth in any one of clauses <1> to <34>, in which the nozzle has a microspace that has a cross-sectional size of 300 μm or more and 1,400 μm or less.

<36>

The method for producing a film as set forth in any one of clauses <1> to <35>, in which the nozzle has a flow path length of 1 mm or more and 25 mm or less.

<37>

The method for producing a film as set forth in any one of clauses <1> to <36>, in which in the electrostatic spraying step, the power supply applies a voltage of 9 kV or more and 30 kV or less to the nozzle to eject the liquid composition at a flow rate of 12 mL/h or less, to thereby perform electrostatic spraying on the surface of the skin, and a ratio of the flow rate (mL/h) to the voltage (kV), flow rate/voltage, is 0.06 or more and 0.6 or less.

EXAMPLES

The present invention will next be described in further detail with reference to examples. However, the scope of the invention is not limited to the examples. Unless otherwise specified, "%" and "part" mean "% by mass" and "part by mass", respectively.

Example 1

(1) Preparation of Liquid Composition

As the component (a) of a liquid composition, 99.5% ethanol (manufactured by Wako Pure Chemical Industries, Ltd.) was used. As the component (b), polyvinyl butyral (manufactured by SEKISUI CHEMICAL CO., LTD., S-LEC B BM-1) was used. As the component (c), ion-exchanged water was used. The mixing ratio of the components is as shown in Table 1. These components were stirred at ordinary temperature for about 12 hours using a propeller mixer to give a homogeneous transparent mixed solution. The solution was used as a liquid composition.

(2) Electrostatic Spraying Step

An electrostatic spray device 10 having the configuration shown in FIG. 1 and FIG. 2 and having the appearance shown in FIG. 4 was used, and the electrostatic spraying method was performed with the electrostatic spray device for 60 seconds toward a skin model (artificial leather, PROTEIN LEATHER PBZ13001BK, manufactured by Idemitsu Technofine Co., Ltd.) cutout into a size of 50 mm×50 mm. The conditions of the electrostatic spraying method was as follows.

Applied voltage: 10 kV

Distance between the nozzle and the skin model: 100 mm

Ejection speed of liquid composition (flow rate): 5 mL/h

Nozzle diameter: 0.3 mm

Environment: 25° C., 40% RH

Examples 2 to 8

The electrostatic spraying step was performed in the same manner as in Example 1 except that the conditions shown in Table 1 were adopted, giving porous films formed of deposited fibers.

Examples 9 and 10

The electrostatic spraying step was performed in the same manner as in Example 1 except that conditions shown in Table 2 were adopted, giving porous films formed of deposited fibers. The conditions of the electrostatic spraying method was as follows.

Applied voltage: 30 kV

Distance between the nozzle and the skin model: 100 mm

Ejection speed of liquid composition (flow rate): 5 mL/h

Nozzle diameter: 0.3 mm

Environment: 25° C., 70% RH

Examples 11 and 12

The electrostatic spraying step was performed using a polyurethane resin (manufactured by Covestro Deutschland AG, Baycusan C2000) as the component (b) in conditions shown in Table 3, giving porous films formed of deposited fibers. The conditions of the electrostatic spraying method was the same as in Example 9.

Comparative Examples 1 and 2

The electrostatic spraying step was performed in the same manner as in Example 9, except that the conditions shown in Table 2 were adopted and that an electrostatic spray device 10 with no voltage stabilizer was used, giving porous films formed of deposited fibers.

[Evaluation of Film Formability]

The electrostatic spray device 10 was charged with the liquid composition prepared at the ratio shown in Table 1 to Table 3, and electrostatic spraying was performed on a skin model for 60 seconds. The film formability was visually evaluated according to the following criteria. The results are shown in Table 1 to Table 3.

good: A film is stably formed for 60 seconds or more.

poor: Spinning is unstable to fail in film formation or to result in a film having unevenness.

[Evaluation of Film Adhesion]

The adhesion of each film formed on a skin model by electrostatic spraying in Examples 1 to 8 was evaluated by rubbing test. Specifically, while a load of about 50 gf was applied with a finger to a film from the upper surface of the film, the film was rubbed five times over a distance of 2 cm in one direction. The adhesion was evaluated in terms of the adhesion state of the film to the application site and the adherence to the finger according to the following criteria.

A: No peeling or breakage of the film or no adherence to the finger is observed.

B: Breakage of the film surface is observed, but no adherence to the finger is observed.

C: Breakage of the film surface is observed, and adherence to the finger is also observed.

D: The film is broken and completely peels off.

TABLE 1

| | Component (% by mass) | Example 1 | Example 2 | Example 3 | Example 4 | Example 5 | Example 6 | Example 7 | Example 8 |
|---|---|---|---|---|---|---|---|---|---|
| (a) | Ethanol | 87.5 | 83 | 70 | 85 | 93 | 84.08 | 88.26 | 88.06 |
| (b) | Polyvinyl butyral (*1) | 10 | 10 | 10 | | 2 | 15 | 11 | 11 |
| | Polyvinyl butyral (*2) | | | | 10 | | | | |
| (c) | Water | 0.5 | 5 | 18 | 5 | 5 | 0.42 | 0.44 | 0.44 |
| (d) | Distearyldimonium chloride (*3) | | | | | | 0.5 | | |
| | Benzalkonium chloride (*4) | | | | | | | 0.3 | |
| | Sodium palmitoyl sarcosinate (*5) | | | | | | | | 0.5 |
| Other component | Glycerol | 2 | 2 | 2 | | | | | |
| | Total amount | 100.0 | 100.0 | 100.0 | 100.0 | 100.0 | 100.0 | 100.0 | 100.0 |
| Mass ratio | Component (b)/component (c) | 20.0 | 2.0 | 0.6 | 2.0 | 0.4 | 35.7 | 25.0 | 25.0 |
| | Component (b)/component (a) | 0.11 | 0.12 | 0.14 | 0.12 | 0.02 | 0.18 | 0.12 | 0.12 |
| | Component (a)/component (c) | 175.0 | 16.6 | 3.9 | 17.0 | 18.6 | 200.2 | 200.6 | 200.1 |
| | Viscosity (mPa · s) | 55.3 | 55.8 | 78.1 | 760.0 | 14.1 | 256.0 | 92.0 | 83.0 |
| | Formability evaluation | good | good | good | good | good | good | good | good |
| | Adhesion evaluation | A | A | A | A | A | A | A | A |

(*1) S-LEC B BM-1 (SEKISUI CHEMICAL CO., LTD.)
(*2) S-LEC B BH-3 (SEKISUI CHEMICAL CO., LTD.)
(*3) VARISOFT TA100 (Evonik Japan)
(*4) NIKKOL CA101 (50% aqueous solution; active amount in Table) (Nikko Chemicals)
(*5) NIKKOL Sarcosinate PN (Nikko Chemicals)

TABLE 2

| | Component (% by mass) | Example 9 | Example 10 | Comparative Example 1 | Comparative Example 2 |
|---|---|---|---|---|---|
| (a) | Ethanol | 88.56 | 84.57 | 88.56 | 84.57 |
| (b) | Polyvinyl butyral (*1) | 11 | 15 | 11 | 15 |
| (c) | Water | 0.44 | 0.43 | 0.44 | 0.43 |
| | Total amount | 100.00 | 100.00 | 100.00 | 100.00 |
| Mass ratio | Component (b)/component (c) | 25.0 | 34.9 | 25.0 | 34.9 |
| | Component (b)/component (a) | 0.12 | 0.18 | 0.12 | 0.18 |
| | Component (a)/component (c) | 201.3 | 196.7 | 201.3 | 196.7 |
| | Viscosity [mPa · s] | 84 | 268 | 84 | 268 |
| | Voltage stabilizer | yes | yes | no | no |
| | Formability evaluation | good | good | poor | poor |

(*1) S-LEC B BM-1 (SEKISUI CHEMICAL CO., LTD.)

TABLE 3

| | Component (% by mass) | Example 11 | Example 12 |
|---|---|---|---|
| (a) | Ethanol | 74.13 | 59.40 |
| (b) | Polyurethane resin (*6) | 25.00 | 39.80 |
| (c) | Water | 0.37 | 0.30 |
| (d) | Distearyldimonium chloride (*3) | 0.50 | 0.50 |
| | Total amount | 100.00 | 100.00 |
| Mass ratio | Component (b)/component (c) | 67.6 | 132.7 |
| | Component (b)/component (a) | 0.34 | 0.67 |
| | Component (a)/component (c) | 200.4 | 198.0 |
| | Voltage stabilizer | yes | yes |
| | Formability evaluation | good | good |

(*3) VARISOFT TA100 (Evonik Japan)
(*6) Baycusan C2000 40% (Covestro Deutschland AG)

As apparent from the results shown in Table 1 to Table 3, the electrostatic spray device used in the present invention can stably form films irrespective of conditions of the ambient environment including humidity. It is also clear that the films formed in Examples 1 to 8 have high adhesion to the skin model.

Reference Example 1

(1) Preparation of liquid composition

As the component (a) of a liquid composition, 99.5% ethanol (manufactured by Wako Pure Chemical Industries, Ltd.) was used. As the component (b), polyvinyl butyral (manufactured by SEKISUI CHEMICAL CO., LTD., S-LEC B BM-1) was used. As the component (c), ion-exchanged water was used. The mixing ratio of the components is as shown in Table 4. These components were stirred at ordinary temperature for about 12 hours using a propeller mixer to give a homogeneous transparent mixed solution. The solution was used as a liquid composition.

(2) Electrostatic spraying step

An electrostatic spray device 10 having the configuration shown in FIG. 1 and having the appearance shown in FIG. 4 was used, and the electrostatic spraying method was performed with the electrostatic spray device for 20 seconds toward a skin model (artificial leather, PROTEIN LEATHER PBZ13001BK, manufactured by Idemitsu Technofine Co., Ltd.) cutout into a size of 50 mm×50 mm. The conditions of the electrostatic spraying method was as follows.

Applied voltage: 30 kV

Distance between the nozzle and the skin model: 100 mm

Ejection speed of liquid composition: 4 mL/h

Nozzle diameter: 0.3 mm

Environment: 25° C., 40% RH

Reference Examples 2 and 3

The electrostatic spraying step was performed in the same manner as in Reference Example 1 except that conditions shown in Table 4 were adopted, giving porous films formed of deposited fibers.

Reference Example 4

The components (a) to (c) and distearyldimonium chloride as component (d) were mixed in the conditions shown in Table 4. The electrostatic spraying step was performed in the same manner as in Reference Example 1, except that the applied voltage was 10 kV and that the ejection flow rate was 5 mL/h, giving a porous film formed of deposited fibers.

Reference Example 5

Polyvinyl butyral and an acrylic acid polymer were used as the component (b), and the components (a) to (c) were mixed in the conditions shown in Table 4. The electrostatic spraying step was performed in the same manner as in Reference Example 1 except that the ejection flow rate was 3 mL/h, giving a porous film formed of deposited fibers.

Reference Example 6

The electrostatic spraying step was performed in the same manner as in Reference Example 1, except that the conditions shown in Table 4 were adopted and that the ejection flow rate was 0.05 mL/h, giving a porous film formed of deposited fibers.

Reference Example 7

The electrostatic spraying step was performed in the same manner as in Reference Example 1, except that the conditions shown in Table 4 were adopted and that the applied voltage was 3 kV, giving a porous film including deposited fibers.

[Evaluation of Film Formability]

The electrostatic spray device 10 shown in FIG. 1 was charged with the liquid composition prepared at the ratio shown in Table 4, and electrostatic spraying was performed on a skin model for 20 seconds. The film formability was visually evaluated according to the following criteria. Table 4 shows the results.

good: A film is stably formed for 1 minute or more.
poor: Spinning is unstable to fail in film formation or to result in a film having unevenness.

As apparent from the results shown in Table 4, the electrostatic spray device used in the present invention can stably form films. It is also clear that the film formed in each example has high adhesion to the skin model.

INDUSTRIAL APPLICABILITY

According to the present invention, a film can be stably formed on skin irrespective of variation in conditions of ambient environment including humidity.

The invention claimed is:

1. A method for producing a film, the method comprising:
   electrostatically spraying a liquid composition directly on a surface of skin using an electrostatic spray device to form the film on the skin, wherein
   the electrostatic spray device includes:
      a container capable of storing the liquid composition,
      a nozzle configured to eject the liquid composition,
      a power supply configured to apply a voltage to the nozzle, and
      a voltage stabilizer configured to stabilize the voltage applied by the power supply to the nozzle,
   the liquid composition contains component (a) and component (b):
      (a) one or more volatile substances selected from alcohols and ketones, and
      (b) a polymer having film formability, and
   in said electrostatic spraying, the liquid composition is electrostatically sprayed on skin using the electrostatic spray device to form a porous film formed of deposited fibers.

2. The method for producing the film according to claim 1, wherein the voltage stabilizer includes:
   a voltage detector configured to detect the voltage applied to the nozzle,
   a comparator configured to compare the voltage detected by the voltage detector to a reference voltage to determine a difference therebetween and to output a signal, and
   a voltage controller configured to control the voltage of the power supply on the basis of the signal output from the comparator.

3. The method for producing the film according to claim 2, wherein
   the liquid composition further contains water as component (c), and

TABLE 4

| | Component (% by mass) | Reference Example 1 | Reference Example 2 | Reference Example 3 | Reference Example 4 | Reference Example 5 | Reference Example 6 | Reference Example 7 |
|---|---|---|---|---|---|---|---|---|
| (a) | Ethanol | 89.5 | 85 | 72 | 84.08 | 84 | 89.5 | 89.5 |
| (b) | Polyvinyl butyral (*1) | 10 | 10 | 10 | 15 | 12 | 10 | 10 |
| | Acrylic acid polymer (*2) | | | | | 3.6 | | |
| (c) | Water | 0.5 | 5 | 18 | 0.42 | 0.4 | 0.5 | 0.5 |
| (d) | Distearyldimonium chloride (*3) | | | | 0.5 | | | |
| | Total amount | 100.0 | 100.0 | 100.0 | 100.0 | 100.0 | 100.0 | 100.0 |
| Mass ratio | Component (b)/component (c) | 20 | 2 | 0.6 | 35.7 | 30.0 | 20.0 | 20.0 |
| | Component (b)/component (a) | 0.11 | 0.12 | 0.14 | 0.18 | 0.14 | 0.11 | 0.11 |
| | Component (a)/component (c) | 179 | 17 | 4 | 200 | 210 | 179 | 179 |
| | Viscosity (mPa · s) | 51.9 | 55.7 | 61.4 | 256 | N.D. | 51.9 | 51.9 |
| | Applied voltage (kV) | 30 | 30 | 30 | 10 | 30 | 30 | 3 |
| | Ejection flow rate (mL/h) | 4 | 4 | 4 | 5 | 3 | 0.05 | 4 |
| | Formability evaluation | good | good | good | good | good | poor | poor |

(*1) S-LEC B BM-1 (SEKISUI CHEMICAL CO., LTD.)
(*2) MAS683, water-insoluble acrylic polymer, CosMED Pharmaceutical Co. Ltd.
(*3) VARISOFT TA100 (Evonik Japan)

a mass ratio of a content of the component (b) to a content of the component (c) is 0.4 or more and 50 or less.

4. The method for producing the film according to claim 2, wherein
the liquid composition further contains water as component (c),
a content of the component (a) in the liquid composition is 50% by mass or more and 94% by mass or less,
the component (b) is dissolvable in the component (a), and
a content of the component (c) in the liquid composition is 0.2% by mass or more and 25% by mass or less.

5. The method for producing the film according to claim 2, further comprising applying, in a direction of the skin, a liquid agent that contains one or more substances selected from water, a polyol, and an oil that is liquid at 20° C., wherein the liquid agent differs from the liquid composition.

6. The method for producing the film according to claim 5, wherein
in said electrostatic spraying, a porous film formed of deposited fibers is formed, and then
in said applying the liquid agent, the liquid agent is applied onto the porous film to form a liquid agent-supporting film in which the liquid agent is supported among the fibers forming the porous film and/or on a fiber surface.

7. The method for producing the film according to claim 5, wherein in said applying the liquid agent, the liquid agent is applied onto the film to maintain transparency of the film.

8. The method for producing the film according to claim 5, further comprising:
applying a cosmetic containing a powder onto a surface of skin,
wherein after said applying the cosmetic said electrostatic spraying is performed.

9. The method for producing the film according to claim 1, wherein the electrostatic spray device further comprises a current limiter configured to stop high voltage generation in the power supply when a current of 2 mA or more flows.

10. The method for producing the film according to claim 1, wherein the electrostatic spray device further includes a housing, and the housing stores the container, the nozzle, the power supply, and the voltage stabilizer and is to be held with a single hand.

11. A method for producing a film, the method comprising:
electrostatically spraying a liquid composition directly on a surface of skin using an electrostatic spray device to form a film on the skin; and
applying, in a direction of the skin, a liquid agent that contains one or more substances selected from water, a polyol, and an oil that is liquid at 20° C., wherein
the electrostatic spray device includes:
a container capable of storing the liquid composition,
a nozzle configured to eject the liquid composition,
a power supply configured to apply a voltage to the nozzle, and
a voltage stabilizer configured to stabilize the voltage applied by the power supply to the nozzle,
the liquid composition contains component (a) and component (b):
(a) one or more volatile substances selected from alcohols and ketones, and
(b) a polymer having film formability, and
the liquid agent differs from the liquid composition.

* * * * *